US011826041B2

(12) United States Patent
Felder

(10) Patent No.: US 11,826,041 B2
(45) Date of Patent: Nov. 28, 2023

(54) BARBED ROD FOR LINEAR TISSUE CLOSURE AND APPROXIMATION

(71) Applicant: John Felder, St. Louis, MO (US)

(72) Inventor: John Felder, St. Louis, MO (US)

(73) Assignee: Washington University, St. Louis, MO (US)

( * ) Notice: Subject to any disclaimer, the term of this patent is extended or adjusted under 35 U.S.C. 154(b) by 38 days.

(21) Appl. No.: 17/671,054

(22) Filed: Feb. 14, 2022

(65) Prior Publication Data

US 2022/0257240 A1    Aug. 18, 2022

Related U.S. Application Data

(60) Provisional application No. 63/148,884, filed on Feb. 12, 2021.

(51) Int. Cl.
*A61B 17/064* (2006.01)
*A61B 17/00* (2006.01)

(52) U.S. Cl.
CPC .. *A61B 17/064* (2013.01); *A61B 2017/00004* (2013.01); *A61B 2017/0641* (2013.01)

(58) Field of Classification Search
CPC ........ A61B 17/064; A61B 2017/00004; A61B 2017/0641; A61B 2017/0461; A61B 2017/00579; A61B 17/56; A61B 17/08; B65H 2701/363; E04H 17/045
See application file for complete search history.

(56) References Cited

U.S. PATENT DOCUMENTS

| | | | | |
|---|---|---|---|---|
| 5,425,747 A | * | 6/1995 | Brotz | A61B 17/08 606/228 |
| 5,584,859 A | * | 12/1996 | Brotz | A61B 17/08 606/228 |
| 6,270,517 B1 | * | 8/2001 | Brotz | A61B 17/064 606/228 |
| 7,468,068 B2 | * | 12/2008 | Kolster | A61B 17/06166 606/228 |
| 7,582,105 B2 | * | 9/2009 | Kolster | A61B 17/06166 606/228 |
| 9,808,234 B2 | * | 11/2017 | Kim | A61B 17/062 |
| 9,872,679 B2 | * | 1/2018 | Perkins | A61B 17/06166 |
| 2007/0162030 A1 | * | 7/2007 | Aranyi | A61B 17/064 606/75 |
| 2009/0012612 A1 | * | 1/2009 | White | A61F 2/30721 606/99 |
| 2009/0248066 A1 | * | 10/2009 | Wilkie | A61B 17/06166 606/228 |
| 2010/0160961 A1 | * | 6/2010 | Nawrocki | A61B 17/06166 606/228 |

(Continued)

*Primary Examiner* — Darwin P Erezo
*Assistant Examiner* — Zehra Jaffri
(74) *Attorney, Agent, or Firm* — POLSINELLI, PC

(57) ABSTRACT

A barbed rod device is provided for tissue closure and approximation. The device includes two or more subassemblies. Each subassembly includes a receiver having a central opening and centerline axis, a plurality of barbs extending radially outward from the receiver, and a linking rod extending from the receiver along the centerline axis of the receiver. The linking rod includes a locking end opposite the receiver. The locking end of a first subassembly is configured to engage the receiver of a second subassembly.

18 Claims, 18 Drawing Sheets

(56) References Cited

U.S. PATENT DOCUMENTS

| | | | |
|---|---|---|---|
| 2011/0288583 A1* | 11/2011 | Goraltchouk | A61B 17/08 606/228 |
| 2016/0051245 A1* | 2/2016 | Spenciner | A61B 17/0401 606/232 |
| 2019/0231351 A1* | 8/2019 | Kim | A61B 17/04 |
| 2019/0282241 A1* | 9/2019 | Haverkost | A61B 17/12172 |
| 2019/0343622 A1* | 11/2019 | Rosenthal | A61L 27/58 |

* cited by examiner

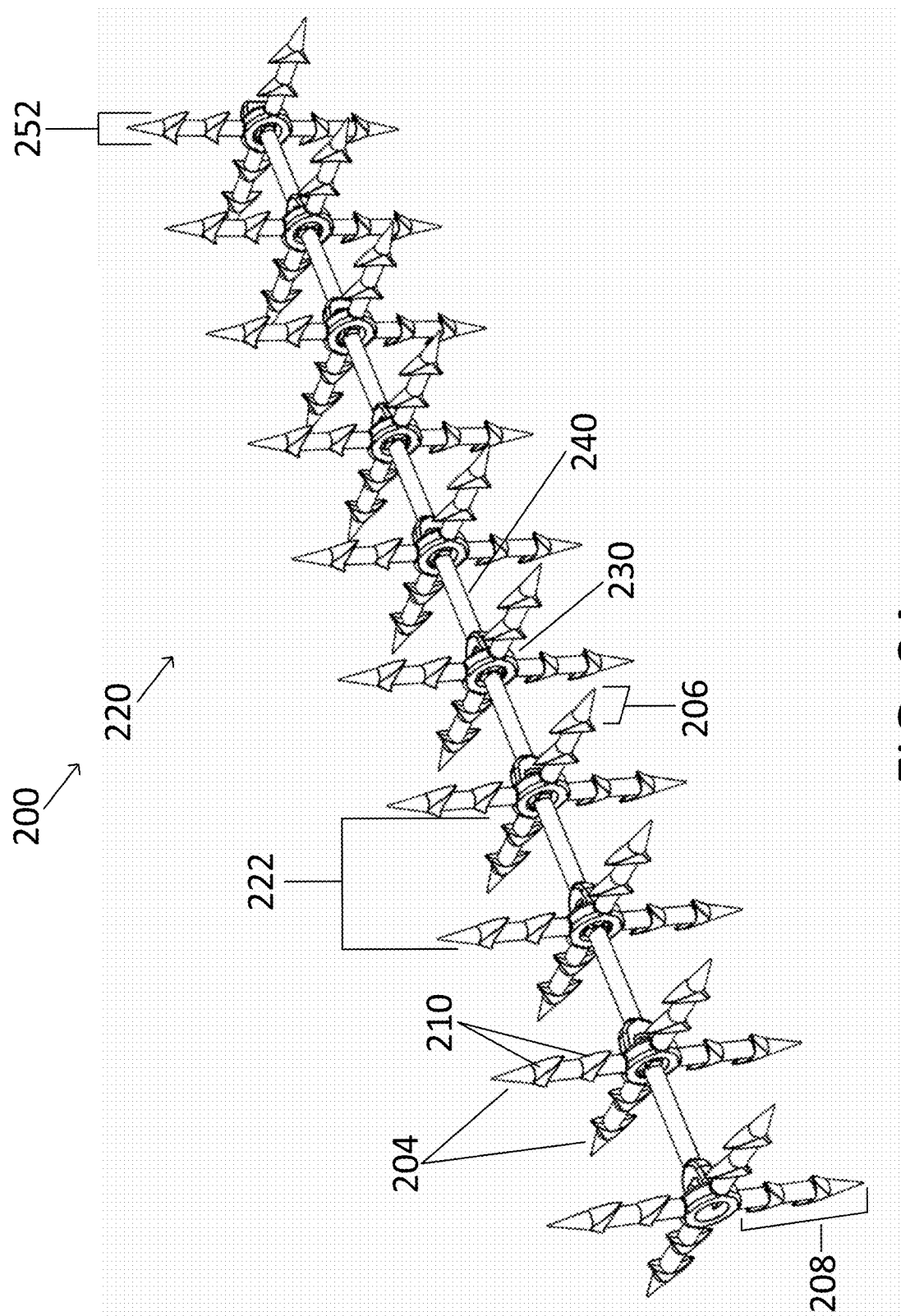

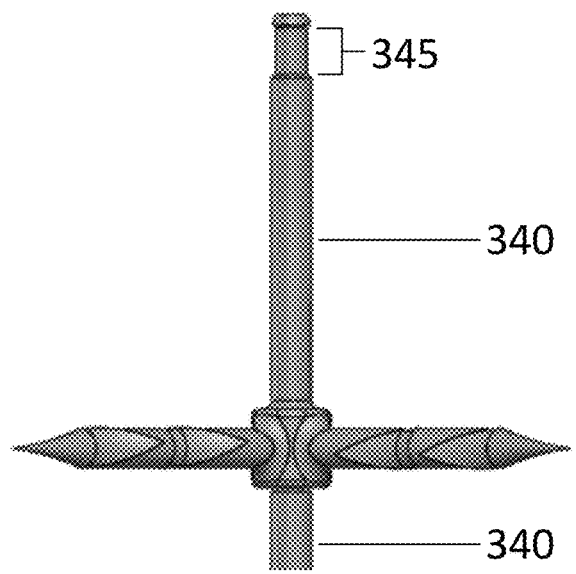
FIG. 13A
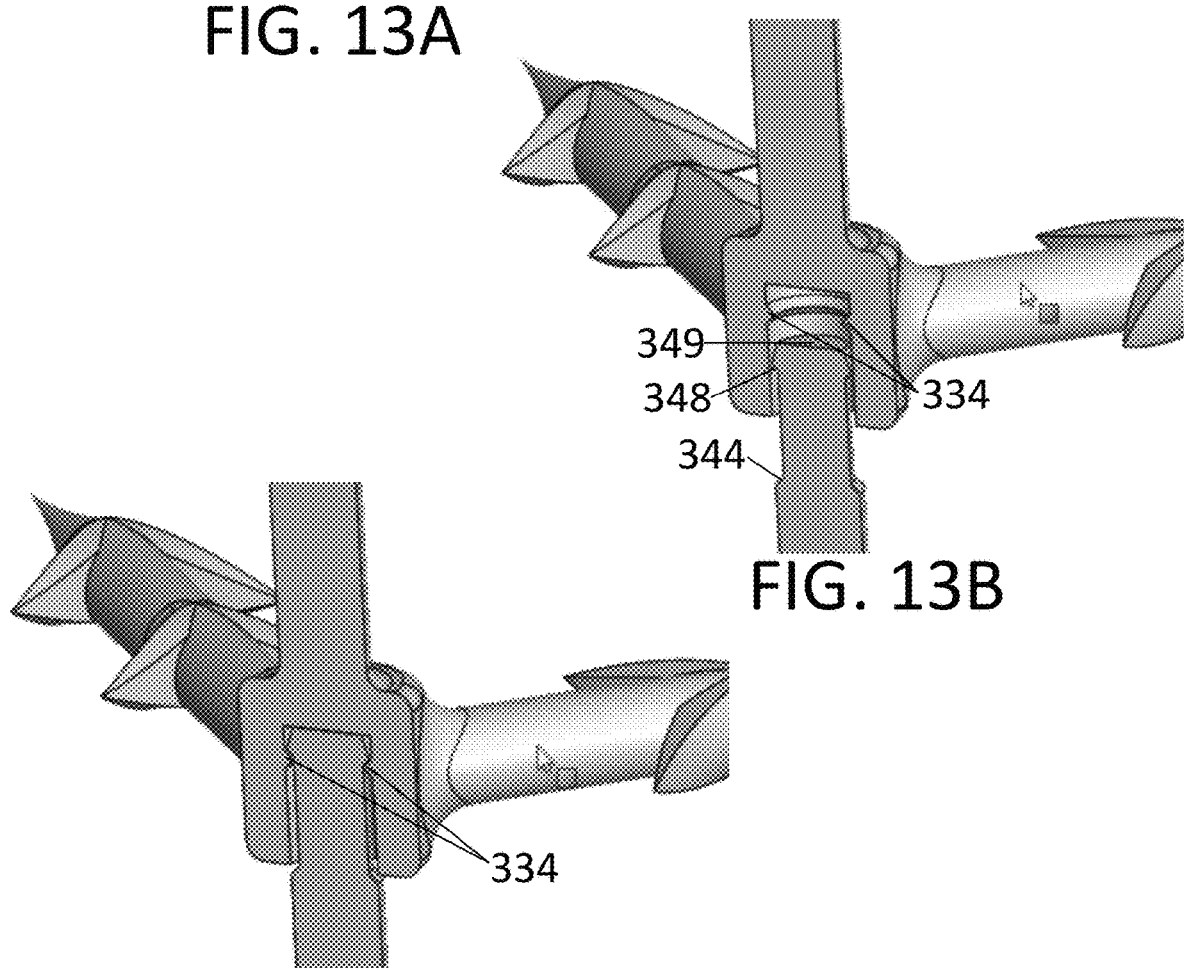
FIG. 13B
FIG. 13C

BARBED ROD FOR LINEAR TISSUE CLOSURE AND APPROXIMATION

CROSS-REFERENCE TO RELATED APPLICATIONS

This application claims priority to U.S. Provisional Application No. 63/148,884, filed Feb. 12, 2021, the contents of which are entirely incorporated by reference herein.

FIELD

The present disclosure relates generally to a barbed rod for soft tissue approximation and closure. In at least one example, the present disclosure relates to a rod with a plurality of self-fixating barbs that may achieve tissue approximation, closure, and stability.

BACKGROUND

Closure of incisions with sutures has long been standard practice. However, using sutures is time-consuming, operator-dependent in its outcome quality, and may require multiple layers of closure, doubling or tripling the effort and time needed for closure of a given length of incision. What is needed is a device that can aid operators in quickly approximating and closing tissue as a replacement for, or a supplement to, sutures.

As presented herein, a barbed rod has been developed to aid in linear closure and approximation of tissue.

BRIEF SUMMARY

Provided herein is a device for tissue closure. The device may include a rod and a plurality of barbs extending from the rod. Each of the plurality of barbs may include a barb body and a plurality of projections.

Further provided herein is another aspect of a device for tissue closure. The device may include two or more subassemblies. Each subassembly may include a receiver having a central opening and centerline axis, a plurality of barbs extending radially outward from the receiver, and a linking rod extending from the receiver along the centerline axis of the receiver. The linking rod may include a locking end opposite the receiver. The locking end of a first subassembly may be configured to engage the receiver of a second subassembly.

The device may be operable to close or approximate tissue subcutaneously, transcutaneously, trans-fascially, trans-muscularly, across ligamentous tissue, across tendinous tissue, or across joint capular tissue. The rod and the plurality of barbs may be biologically resorbable and be made of polyglactin, polydioxanone, polyglecaprone, polyhydroxy-butyrate, calcium compounds, or other resorbable materials. Additionally, the device may be coated with resorbable materials such as magnesium. The device may also be made of titanium, nitinol, steel, or other non-resorbable materials. Each of the plurality of barbs may have a plurality of projections that are angled toward the rod. The plurality of barbs may be placed along the rod in groups, wherein the number of barbs per group may vary. The size of the device may vary depending on the application. In some embodiments, one of the plurality of barbs may have a blunted end.

Also disclosed herein is a method of tissue closure and approximation using the barbed rod or barbed rod assembly device. The method may include placing the device inside an opened tissue and then pressing the edges of the opened tissue onto the device, wherein the plurality of barbs penetrate and are retained within the tissue. The method may further include pushing the device downward into tissues below the opened tissue.

Other aspects and iterations of the invention are described more thoroughly below.

BRIEF DESCRIPTION OF THE DRAWINGS

Implementations of the present technology will now be described, by way of example only, with reference to the attached figures, wherein:

FIG. 3A is an isometric view of a barbed rod assembly for linear tissue closure including subassemblies with twist and lock coupling mechanisms.

FIG. 13A is a top view of a subassembly coupled with a portion of a second subassembly after engagement of the snap and lock coupling mechanism.

FIG. 13B is a perspective, cross-sectional view of a portion of two subassemblies prior to engagement of the snap and lock coupling mechanism.

FIG. 13C is a perspective, cross-sectional view of a portion of two subassemblies after engagement of the snap and lock coupling mechanism.

DETAILED DESCRIPTION

Figure 1:
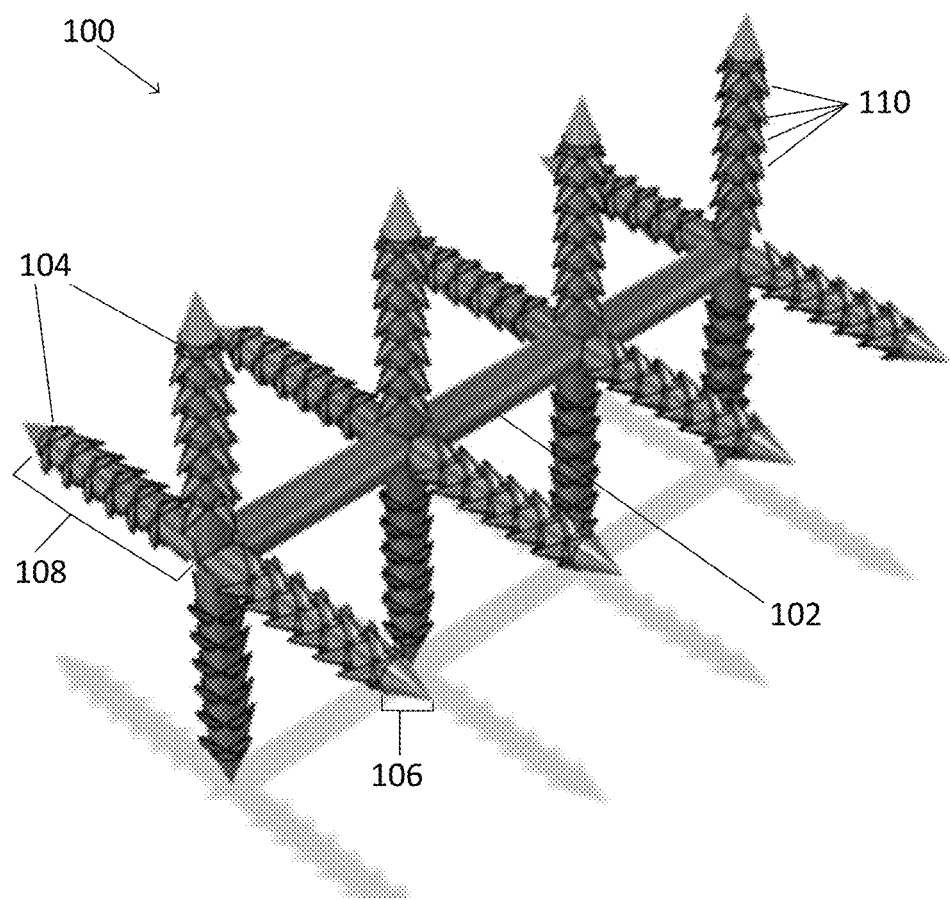
FIG. 1 is a perspective view of an example prefabricated barbed rod for linear tissue closure.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

As used herein, the terms "comprising," "having," and "including" are used interchangeably in their open, non-limiting sense. The terms "a," "an," and "the" are understood to encompass the plural as well as the singular. Thus, the term "a mixture thereof" also relates to "mixtures thereof."

Generally, the ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc. Other than in the operating examples, or where otherwise indicated, all numbers expressing quantities of ingredients and/or reaction conditions may be modified in all instances by the term "about," meaning within +/−5% of the indicated number.

The terms "coupled" and "attached" are defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims or can be learned by the practice of the principles set forth herein.

Figure 2:
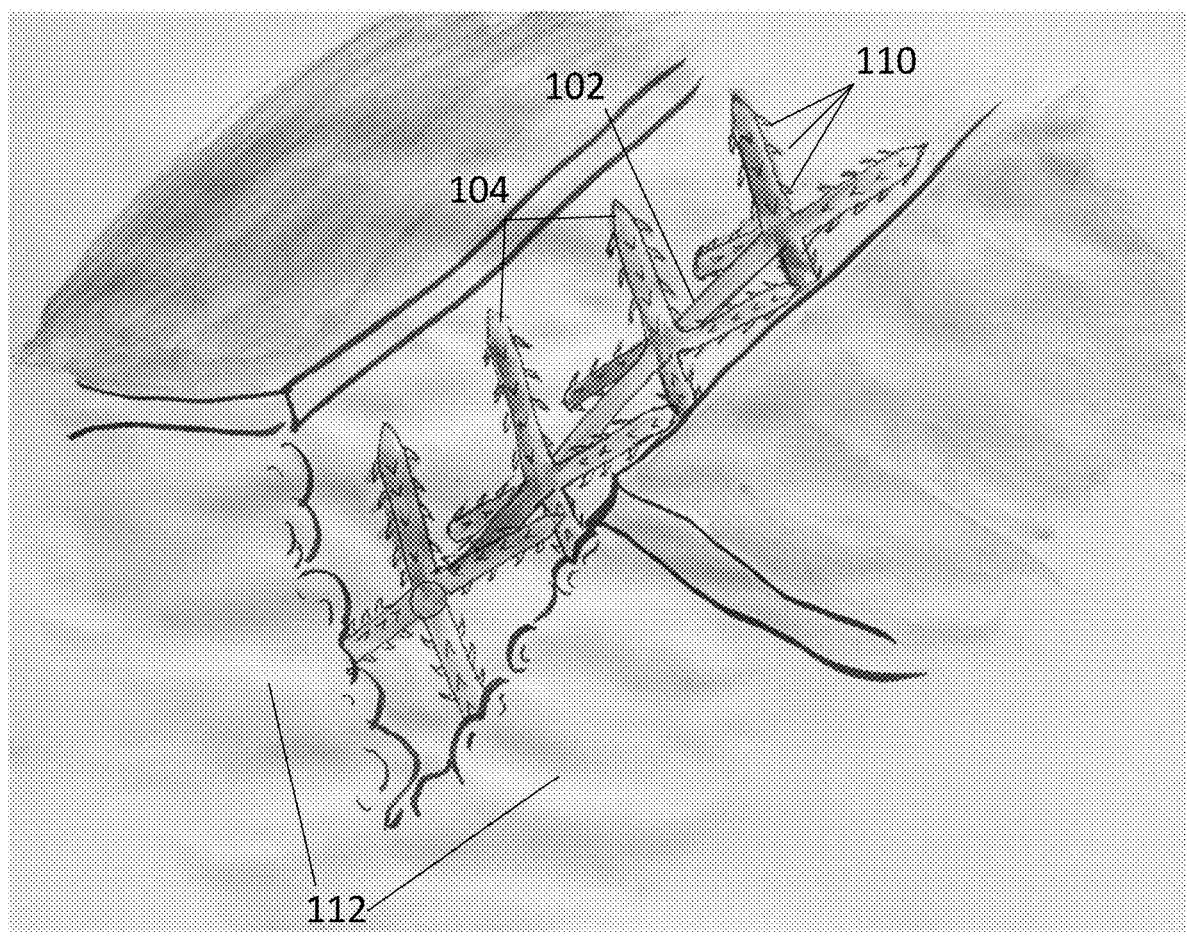
FIG. 2 is an example prefabricated barbed rod for linear tissue closure placed in opened tissue.
Figure 3B:
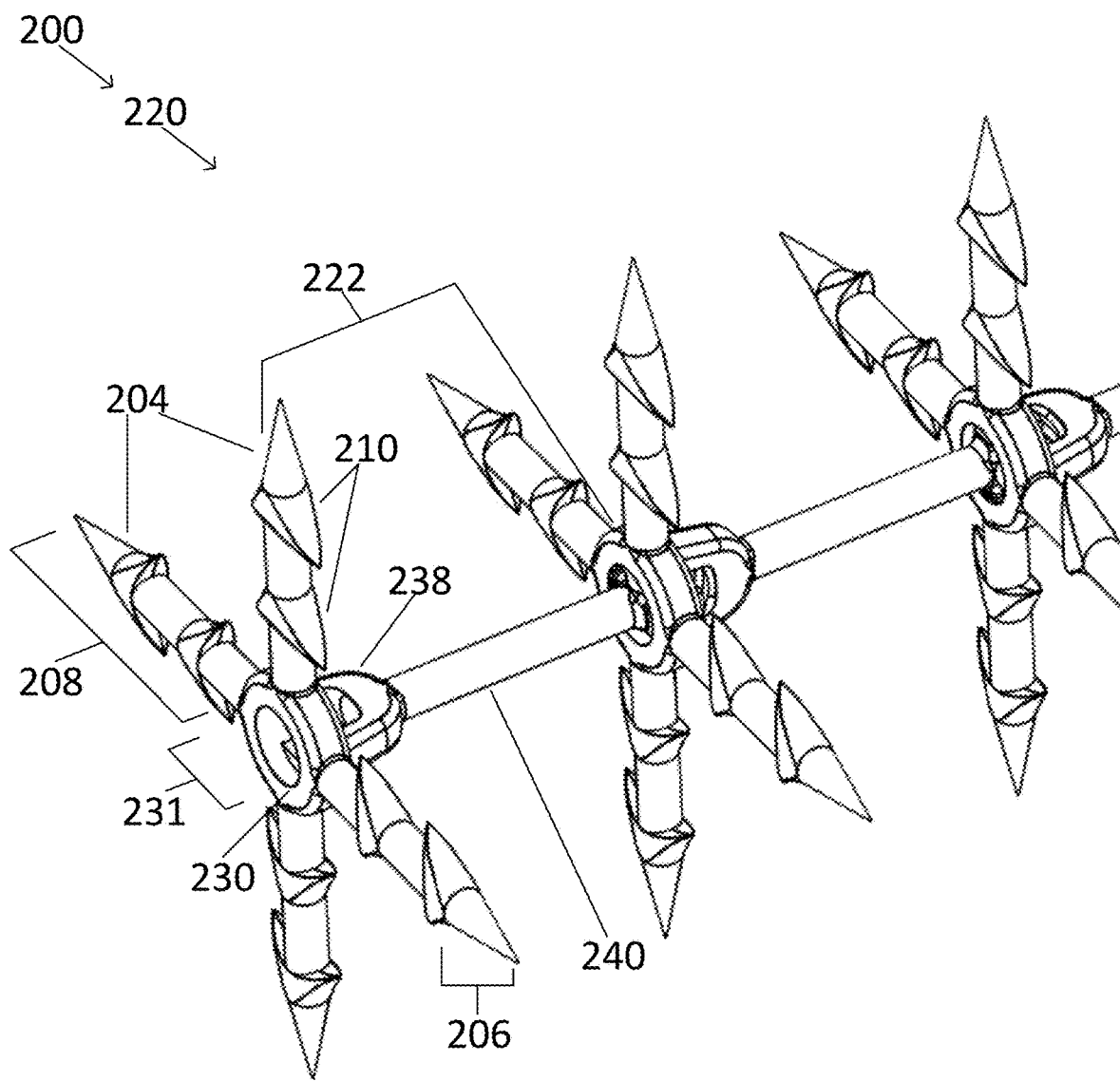
FIG. 3B is another isometric view of a barbed rod assembly for linear tissue closure including subassemblies with twist and lock coupling mechanisms.
Figure 3C:
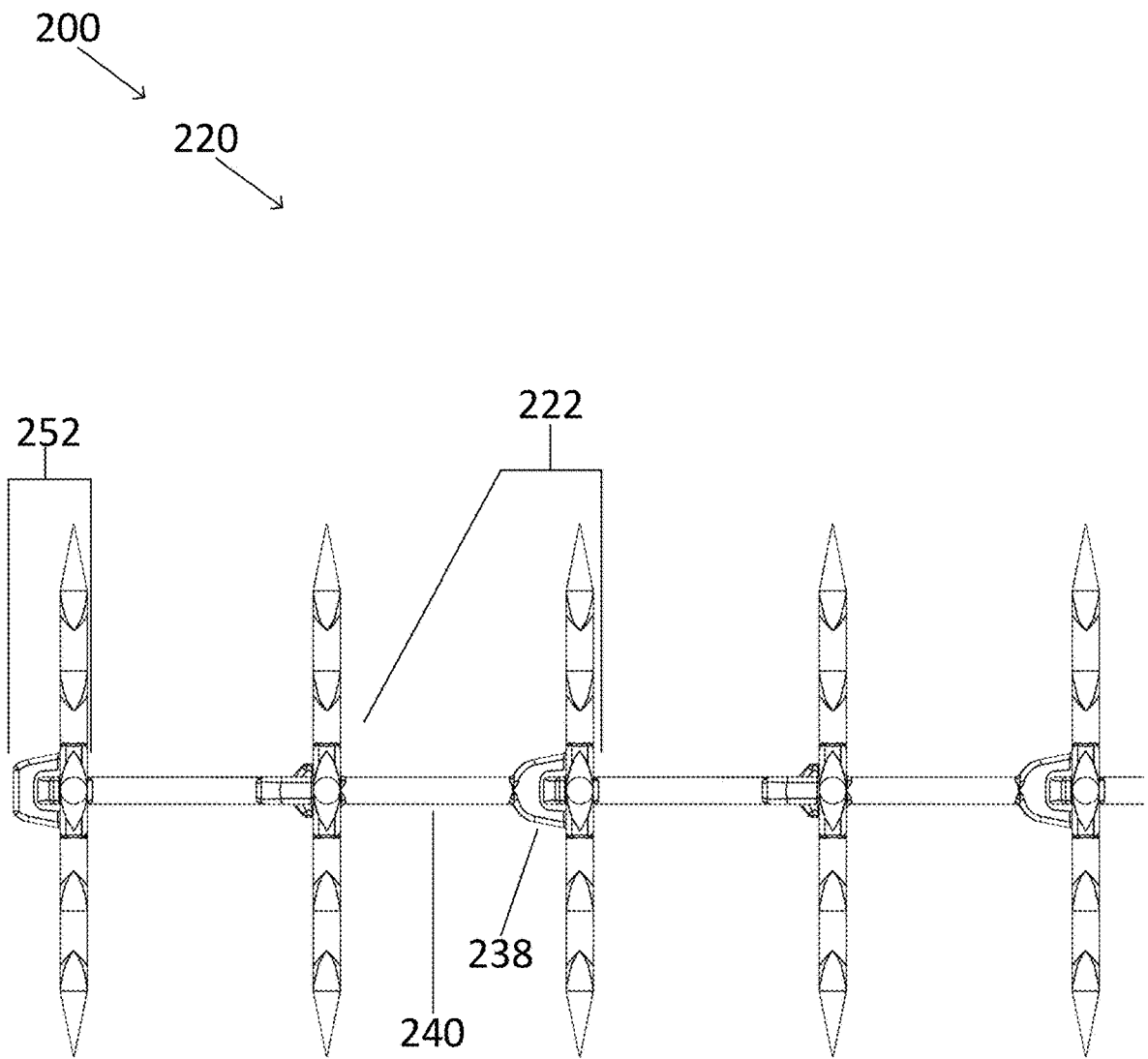
FIG. 3C is a side view of a barbed rod assembly for linear tissue closure including subassemblies with twist and lock coupling mechanisms.
Figure 4A:
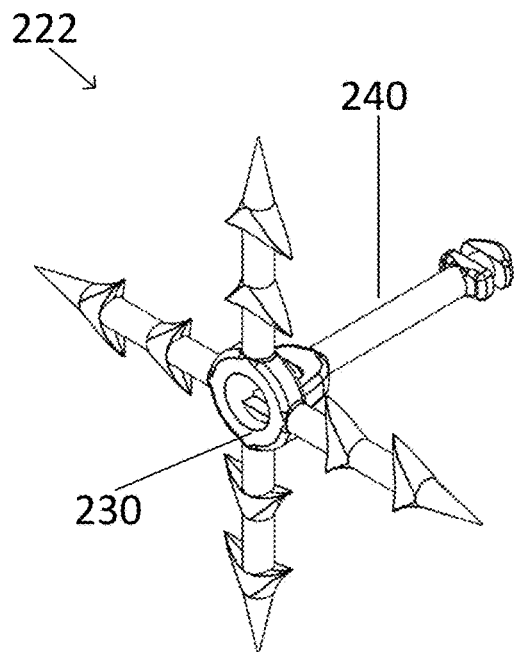
FIG. 4A is an isometric view of a subassembly with a twist and lock coupling mechanism.
Figure 4B:
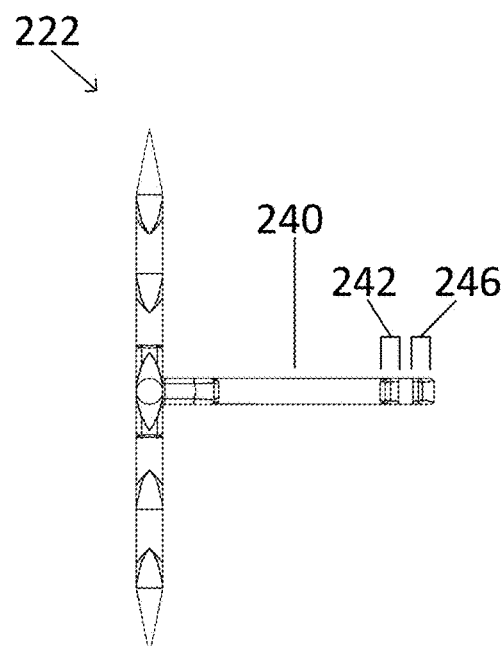
FIG. 4B is a side view of a subassembly with a twist and lock coupling mechanism.
Figure 4C:
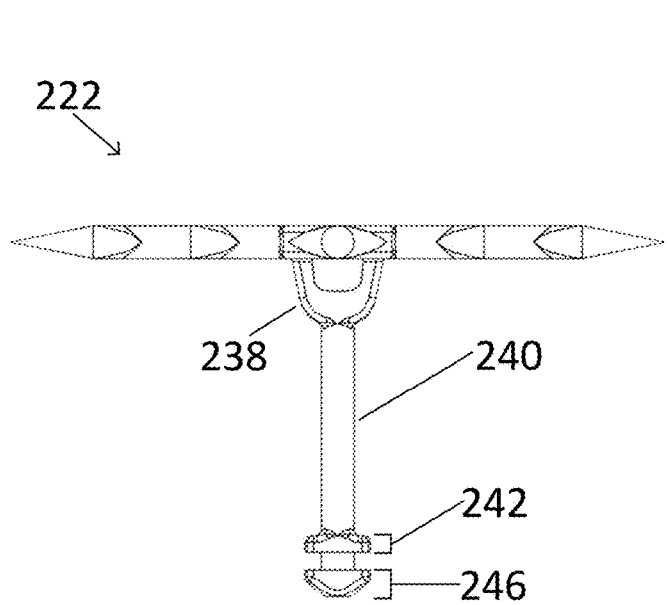
FIG. 4C is a top view of a subassembly with a twist and lock coupling mechanism.
Figure 4D:
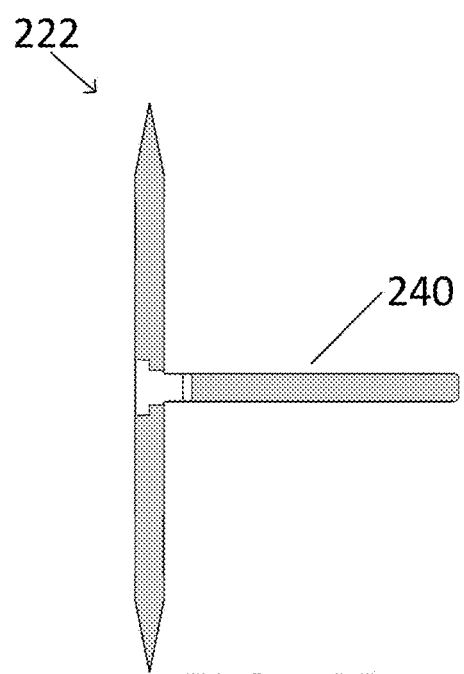
FIG. 4D is a cross-sectional view of a subassembly with a twist and lock coupling mechanism.
Figure 5A:
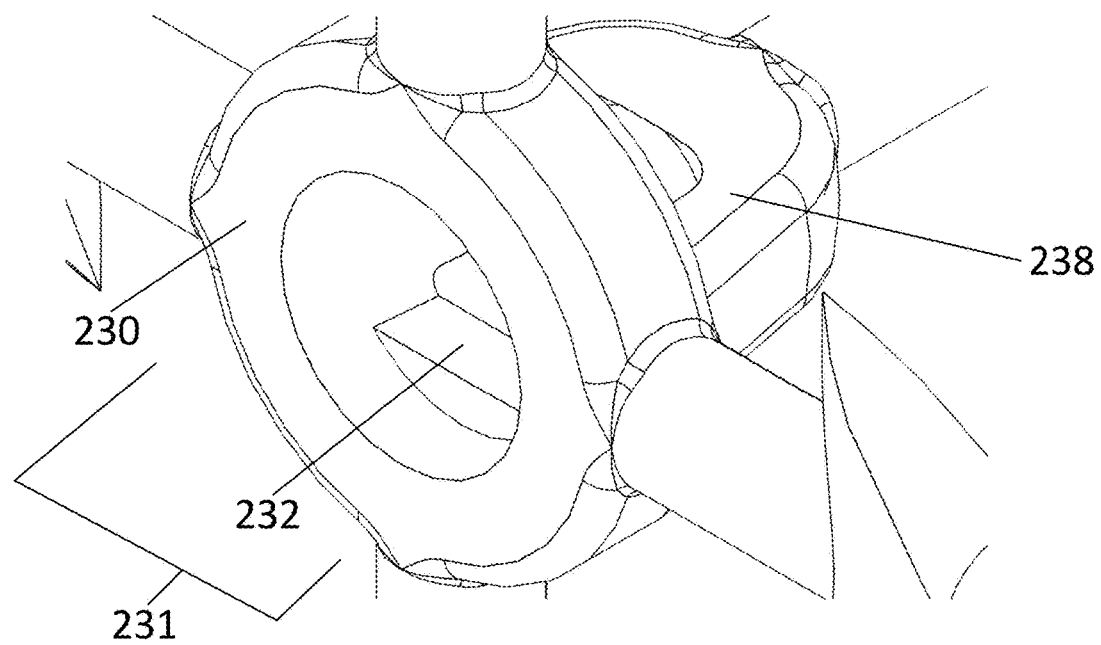
FIG. 5A is an isometric view of the receiver of a subassembly with a twist and lock coupling mechanism.
Figure 5B:
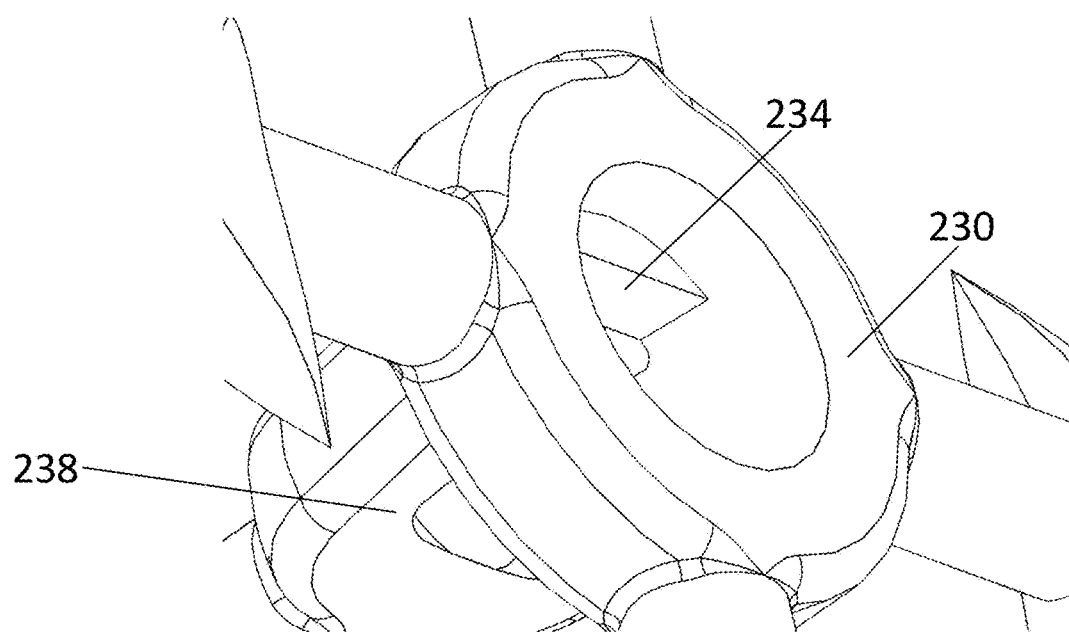
FIG. 5B is a perspective view showing the front side of the receiver of a subassembly with a twist and lock coupling mechanism.
Figure 5C:
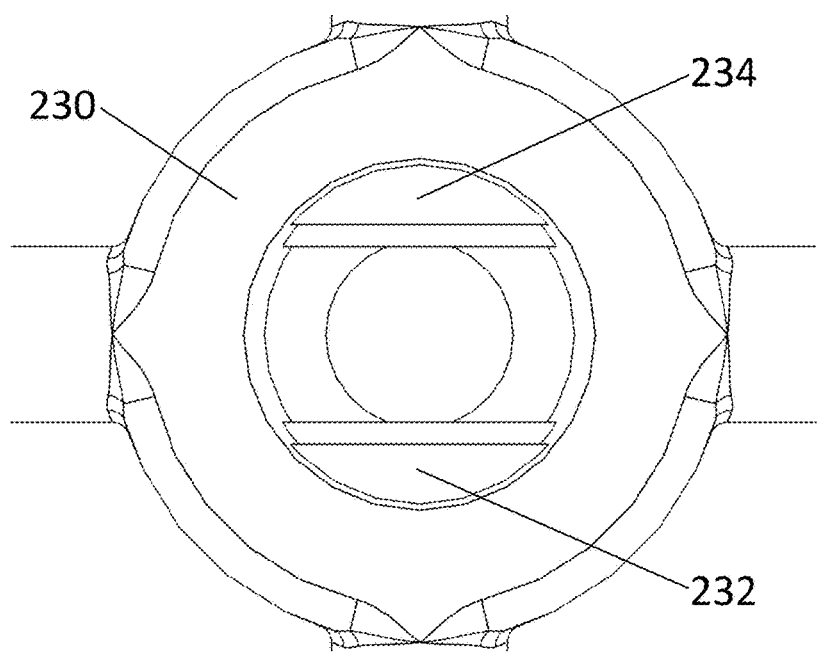
FIG. 5C is a front view of the receiver of a subassembly with a twist and lock coupling mechanism.
Figure 5D:
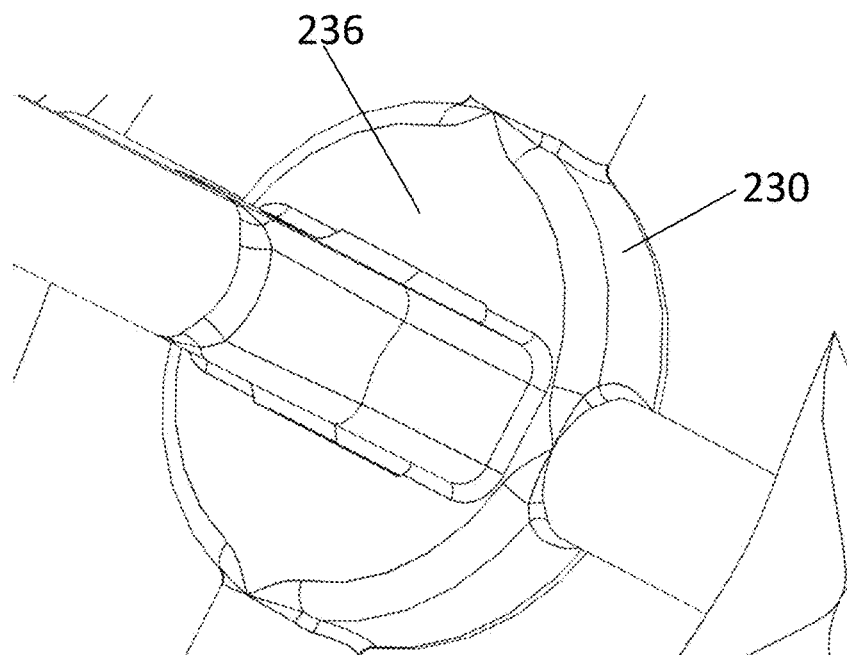
FIG. 5D is a perspective view showing the back side of the receiver of a subassembly with a twist and lock coupling mechanism.
Figure 6A:
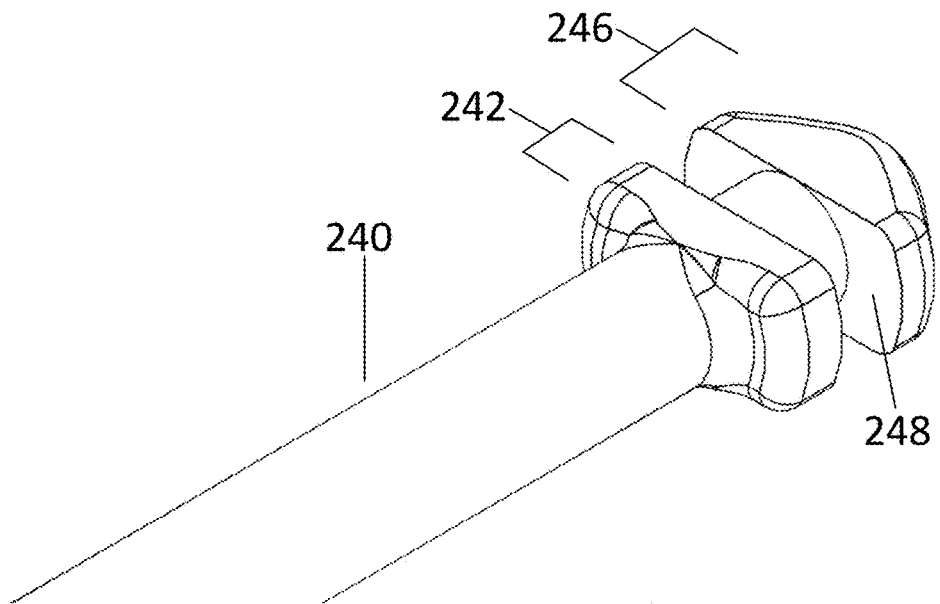
FIG. 6A is an isometric view of the locking end of the linking rod of a subassembly with a twist and lock coupling mechanism.
Figure 6B:
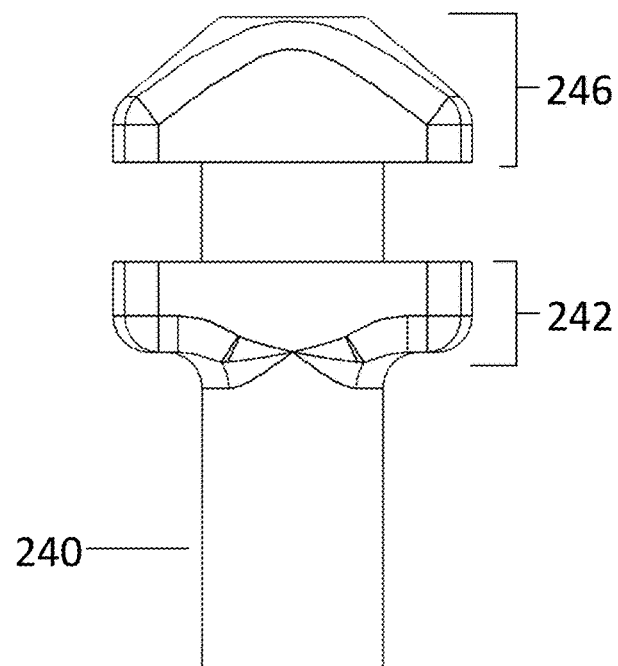
FIG. 6B is a top view of the locking end of the linking rod of a subassembly with a twist and lock coupling mechanism.
Figure 6C:
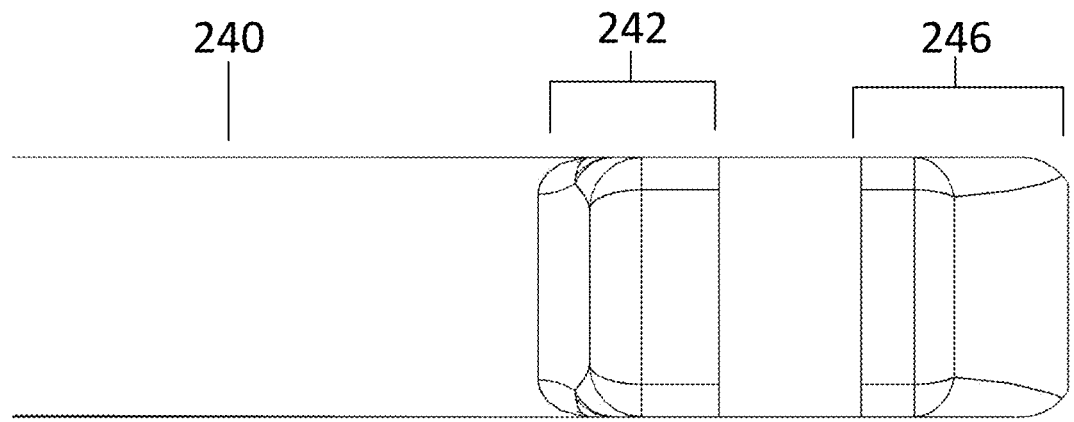
FIG. 6C is a side view of the locking end of the linking rod of a subassembly with a twist and lock coupling mechanism.
Figure 6D:
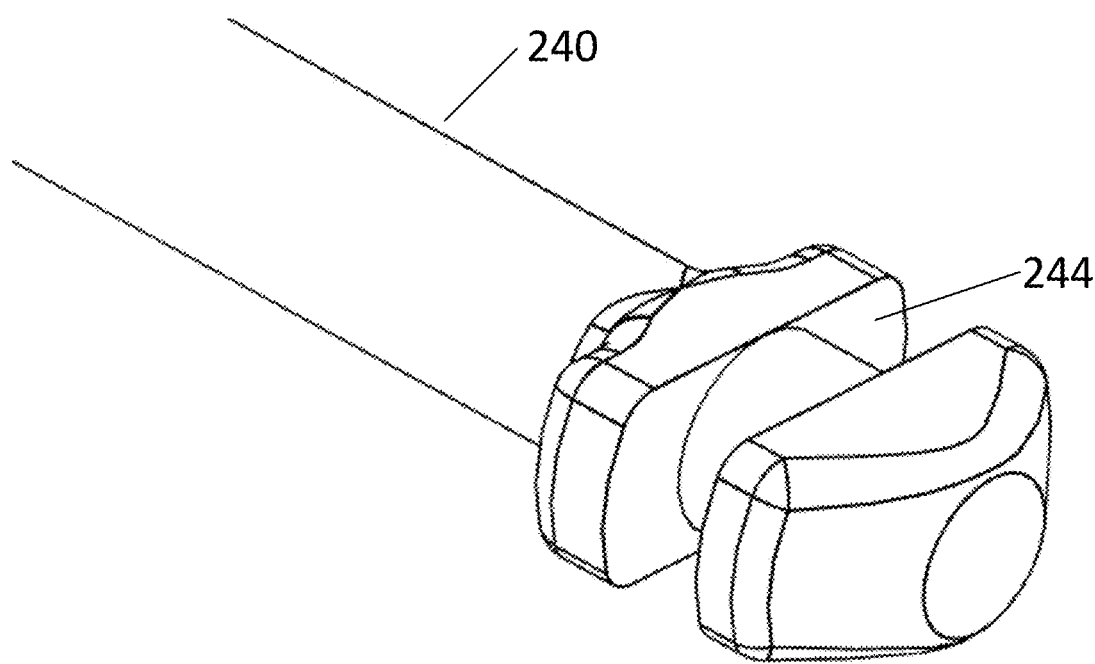
FIG. 6D is a perspective view of the locking end of the linking rod of a subassembly with a twist and lock coupling mechanism.

Provided herein is a barbed rod device for wound closure and approximation for use in conjunction with or as an alternative to sutures. The device is a rod designed to stably fixate soft tissues in an approximated position. In an embodiment, as seen in FIGS. 1 and 2, the device may include a rod with affixed barbs that penetrate and adhere to tissues. In other embodiments, as seen in FIGS. 3A to 14C, the device may be modular, whereby barbed rod assemblies contain subassemblies that are coupled or mated together. Each subassembly includes a linking rod and a receiver with affixed barbs that penetrate and adhere to tissues. The barbs may additionally have affixed projections that penetrate and adhere to tissues. In various examples, the barbed rod device may be used for subcutaneous skin closure, transcutaneous skin closure, closure across fascial planes, or fixing superficial tissue layers to deeper tissue layers (e.g., fixing subcutaneous tissue flaps down to underlying fascia).

The barbed rod device may achieve tissue approximation, stability, and closure, without the wasted time and variability of suturing. In some examples, the barbed rod may reduce operating room time, reduce time required for tissue approximation, reduce effort required to complete repetitive or mundane portions of procedures, reduce complications such as wound dehiscence that are associated with mechanical limitations of traditional sutures distribute tension easily across a tissue closure, fix multiple tissue layers at once, reduce dead space in thick subcutaneous tissue, provide three-dimensional stability of tissues, reduce interoperator variability, or prepare deeper layers of tissue for superficial closure (e.g., approximating dermis and subcutaneous tissue with the barbed rod device so that only tissue adhesives or other epidermal closure devices except for sutures are needed to close epidermal tissue).

The barbed rod device may have significant advantages over traditional sutures, as a single-step application would approximate or close an entire incision, potentially replacing the need for multiple sutures. Multiple tissue planes may all be approximated with one application (e.g. with barbs that penetrate deeply), as opposed to devices such as staples that only approximate the dermis but allow deeper layers of tissue to pull away from one another. The cumulative time savings in the operating room would be significant during a day, week, or month, and the devices themselves would amount to a financial resource, as operating room time is very expensive. The barbed rod device also has advantages over sutures because it provides three-dimensional stability and distribution of tension (i.e., tension is transmitted into the framework of the barbed rod device more so than across tissues as compared with sutures). It would expedite the process of wound closure, reduce operator variability, or reduce the likelihood of dehiscence.

As seen in FIGS. 1 and 2, the barbed rod 100 includes a rod 102 and plurality of barbs 104 that may extend outward from the rod 102. Each of the plurality of barbs 104 comprises a barb body 108, which includes a plurality of projections 110 placed along the barb body 108 and angled toward the rod 102. In some embodiments, each of the plurality of barbs 104 includes a tapered end 106.

The barbed rod may have a generally circular, elliptical, square, rectangular, or ovular cross-section. The barbed rod may be provided in multiple sizes and may be able to be "cut to fit" such that a larger piece can be cut to fit a smaller need. In some examples, the barbed rod device may be packaged in a spool or in individual packages, such as boxes. In other examples, the barbed rod device may be modular in that the rod may have openings in it operable to receive barbs. The barbs may then be mated to the openings in the rod. The diameter of the barbed rod 100—as measured from the tip of one barb to the tip of a barb on the opposite side of the rod—may range from about 1 mm to about 100 mm. For example, the barbed rod may have a diameter of 1-5 mm, 5-10 mm, 10-15 mm, 15-20 mm, 20-25 mm, 25-30 mm, or 30-35 mm, 35-40 mm, 40-45 mm, 45-50 mm, 55-60 mm, 60-65 mm, 65-70 mm, 70-75 mm, 75-80 mm, 80-85 mm, 85-90 mm, 90-95 mm, or 95-100 mm. In other embodiments, the barbed rod may have a diameter ranging from 1-5 mm. In one example, a small barbed rod only 3-4 mm in diameter may be used to accommodate closure of thin tissues such as on the forearm or other areas where skin is thin. In another example, a larger barbed rod 4-5 cm in diameter may be used to accommodate closure of thick tissues such as on the abdomen or other areas where skin is thick.

The barbed rod 100 may be used to close separated tissue. For example, as seen in FIG. 2, the barbed rod 100 may be placed inside open tissue such that the barbs 104 make contact with tissue 112. In some examples, the tissue 112 may then be pressed against the barbs 104 such that the barbs penetrate and self-adhere to the tissue. In some examples, the barbed rod 100 may be pressed into the tissue 112 such that the barbs penetrate and self-adhere to the tissue.

The barbed rod may be biologically resorbable with varying tensile strength and elasticity/rigidity characteristics for various applications. In at least one example, the barbed rod is biodegradeable. The barbed rod may be made of polyglactin, polydioxanone, polygelcaprone, poly-hydroxybutyrate, calcium compounds (e.g., calcium sulfate, calcium hydroxyapatite, or other calcium compounds), or other resorbable materials. In some instances, parts or all of the barbed rod may also be coated with metals, such as magnesium, titanium, nitinol, steel, and/or other biologically resorbable metals, to impart rigidity, tissue penetration, handling characteristics, texturing, friction, or to provide a joining or locking mechanism to configure the barbs and rods in a modular embodiment of the device. Use of metals may also allow the barb to be bent or deformed into another angle or configuration. In one example, nitinol is used to allow the device to recoil to its original shape after the device is deformed. In some aspects, the biodegradable barbed rod may last less than two weeks, two weeks, one year, or longer, or any other duration before being resorbed. In another example, the barbed rod is permanent, i.e., not biodegradable. In such examples, the permanent rod may be made of polypropylene, nylon, or another non-biodegradable material. In yet another example, the rod is biodegradable and the barbs are permanent. In still another example, the rod is permanent and the barbs are biodegradable. In some embodiments, materials such as antibiotics or other drugs may be impregnated into the device.

Attached or connected to the rod 102 are a plurality of rigid or semi-rigid barbs 104 that penetrate and self-adhere to tissue. The barbs may be evenly spaced along the rod, spaced in a pattern along the rod, or could be randomly spaced. The barbs may be straight, or they may bend or have sharp angles along the barb body. As seen in FIGS. 1-2, the barbs 104 may be placed in groups along the rod 102, or could be placed individually along the rod 102. For example, a group of barbs 104 may include 2, 3, 4, 5, or 6 barbs. In one example, each group of barbs alternates direction along the rod, i.e. one group oriented horizontally and the next group oriented vertically. The group of barbs 104 may be evenly spaced, circumferentially, around the rod 102. In at least one example, a group of barbs 104 includes 4 barbs extending radially out from the rod 102 and spaced 90° from each other around the rod 102. In some examples, a first group of barbs 104 may be spaced a set distance from a second group of barbs 104. The set distance may be about 1-20 mm. For example, a first group of barbs may be spaced 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm from a second group. The barbs 104 may extend from the rod 102 at an angle relative to the rod of less than or equal to 90 degrees. For instance, the barbs 104 may extend from the rod at an angle of about 30°, 35°, 40°, 45°, 50°, 55°, 60°, 65°, 70°, 75°, 80°, 85°, or 90°.

In one embodiment, the barbs and the rod are modular. In one aspect, the modular barbs may come in a set, wherein the set of barbs may be fixed at any point along the rod. In one example, the set of barbs has a central opening that may be transfixed by the rod. In another example, the set of barbs has a central aperture that may be opened and placed along the rod at a given location, and then the aperture may be reversibly or irreversibly closed around the rod by a mechanical recoil, a snapping mechanism, peg system, threads and screws, or another joining mechanism. In another aspect, the modular rod may have a plurality of openings operable to receive the barbs. In one example, the barbs lock into the plurality of openings by a mechanical recoil, a snapping mechanism, a peg system, threads and screws, or another joining mechanism. In some examples, the barbs may be attached to the rod at an angle. In some examples, the joining mechanism may comprise a nonresorbable material to better facilitate joining the barbs to the rod and provide structural stability. The barbs may be manufactured separately from the rest of the device. Some methods for manufacturing the barbs may include injection molding. In some examples, the barbs may be manufactured and then later joined to the rod via an injection mold while keeping the barbs positionally stable, an adhesive, or other methods of attachment.

As seen in FIGS. 1-2, the barbs 104 may include a barb body 108, one or more projections 110 or smaller sub-barbs emanating from the barb body 108, and a tapered portion 106 ending at a point that is sufficient to pierce tissue. Projections 110 may extend from the barb body, from the tapered portion, or both. In some embodiments, each end of the rod may also comprise a plurality of projections. In some embodiments, the tapered portion 106 may be replaced with a flat or blunted portion depending on the application and need. For instance, a barb blunted portion may be used to provide stability for the device. In some examples, the projections 110 may allow for the barb to be securely fixated in the tissues and provide resistance to pull out the barb from the penetrated tissues. The barbs 104 may be used in various quantities and concentrations along the rod. In some embodiments, the barbs are placed asymmetrically in relation to a cross-sectional perspective of the rod.

The barbs and projections may vary in type, quantity, thickness, length, angle, shape, spacing, or direction with various projection configurations. For example, the barbs may be round, triangular, or rectangular/prism-shaped, blade-like, curved, tooth-like, or may assume other similar forms. For example, the barbs may have a shape that allows tissue to be penetrated but not severed. The barbs may have a shape to optimize the stability of the barbs. For instance, the barbs may be wider at their base where they project from the rod and taper to a smaller diameter at the point of the barb to facilitate tissue penetration. The projections may be angled toward the rod to facilitate the barb's self-adherence to the tissue.

The barbs may have a length ranging from about 0.25-100 mm. In some examples, the barbs have a length of about 0.25-10 mm, 10-20 mm, 20-30 mm, 30-40 mm, 40-50 mm, 50-60 mm, 60-70 mm, 70-80 mm, 80-90 mm, or 90-100 mm. The barbs may have a diameter ranging from 0.25-15 mm. In some examples, the barbs have a diameter of 0.25-1 mm, 1-2 mm, 2-3 mm, 3-4 mm, 4-5 mm, 5-6 mm, 6-7 mm, 7-8 mm, 8-9 mm, 9-10 mm, 10-11 mm, 11-12 mm, 12-13 mm, 13-14 mm, or 14-15 mm. In some embodiments, the barbs have a length of about 3-4 mm and a diameter of about 0.7-1 mm. In other embodiments, the barbs have a length ranging from 0.25-20 mm. The barbs may have variable lengths and diameters depending on the application for the barbed rod. The operator may choose the appropriate length and diameter based on the particular patient and situation at hand. For example, closing the skin and subcutaneous fat of a patient with a BMI of 25 would require shorter length barbs, while a patient with a BMI of 40 may require longer length barbs. Considerations for choosing the dimensions of the barbs include the thickness of the skin or subcutaneous tissues in the area of the body where the device is to be used.

The projections may extend radially from each barb. In some examples, the projections may extend at an angle from the barb body. Each of the plurality of projections may extend at an angle of less than or equal to 90 degrees from the barb body. For example, the projection may extend from the barb body at an angle of 15°, 20°, 25°, 30°, 35°, 40°, 45°, 50°, 55°, 60°, 65°, 70°, 75°, 80°, 85°, or 90°. The projections may have a tip that points towards the rod or away from the rod. In one embodiment, the projections are angled at 45 degrees toward the rod in relation to the barb body. This may result in projections on different barbs pointing in different directions. For example, as seen in FIGS. 1-2, the tips of the projections on the barbs all point towards the rod, such that barbs that are on opposite sides of the rod have projections that are pointing in opposite directions.

The projections may be macroscopic, shaped projections, or may be a textured surface added to the barb body by, for example, cutting or coating with another material that serves to generate resistance to pull-out. In some examples, the projections may be about 0.25 mm to about 10 mm in length. In some examples, the length of the projections may be about 0.25-1 mm, 1-2 mm, 2-3 mm, 3-4 mm, 4-5 mm, 5-6 mm, 6-7 mm, 7-8 mm, 8-9 mm, or 9-10 mm. In at least one example, the projections may be less than 1 mm in length. In some examples, the barb projections may be cut into the material of the barb body. In additional examples, the barb projections may be fabricated by, for example, an injection mold technique, 3D printing, stereolithography, or laser-cutting. The projections may be created by the same methods as the barb body, by subtraction or precipitation, or by coating with a material generating a roughened surface. The projections may be macroscopic, shaped projections as depicted in FIGS. 1-2, or may be a textured surface added to the barbs by, for example, cutting, rasping, or coating (with another material) which serves to generate resistance to pull-out as the macroscopic projections would.

In another embodiment, as shown in FIGS. 3A to 9B, the barbed rod 200 may be a modular barbed rod assembly 220. Sets of barb subassemblies 222 can be coupled together by twist and lock mechanisms incorporated into each subassembly 222 to form the modular barbed rod assembly 220. Referring to FIG. 3B, each subassembly 222 contains a plurality of barbs 204 extending radially outward from a receiver 230, a receiver extension 238 extending around a central opening 231 of the receiver 230, and a linking rod 240 comprising a receiver end and a locking end opposite the receiver end, wherein the receiver end of the linking rod 240 is connected to the receiver extension 238 and the locking end of the linking rod 240 extends laterally outward along the centerline axis of the receiver 230 to the locking end. The linking rod 240 may have a generally circular, elliptical, square, rectangular, or ovular cross-section. Each of the plurality of barbs 204 comprises a barb body 208, which includes a plurality of projections 210 placed along the barb body 208 and angled toward the receiver 230. In some embodiments, each of the plurality of barbs 204 includes a tapered end 206.

The subassemblies 222 may be provided in multiple sizes. In some examples, subassemblies 222 may be coupled together and packaged as barbed rod assemblies 220 of various lengths. In other examples, the barbed rod assemblies may contain additional modularity in that the linking rod may have openings in it operable to receive barbs. The barbs may then be mated to the openings in the linking rod. The diameter of the barbed rod assembly—as measured from the tip of one barb to the tip of a barb on the opposite side of the receiver—may range from about 1 mm to about 100 mm. For example, the barbed rod assembly may have a diameter of 1-5 mm, 5-10 mm, 10-15 mm, 15-20 mm, 20-25 mm, 25-30 mm, or 30-35 mm, 35-40 mm, 40-45 mm, 45-50 mm, 55-60 mm, 60-65 mm, 65-70 mm, 70-75 mm, 75-80 mm, 80-85 mm, 85-90 mm, 90-95 mm, or 95-100 mm. In one example, a small barbed rod assembly only 3-4 mm in diameter may be used to accommodate closure of thin tissues such as on the forearm or other areas where skin is thin. In another example, a larger barbed rod assembly 4-5 cm in diameter may be used to accommodate closure of thick tissues such as on the abdomen or other areas where skin is thick. The length of the subassembly 222 may range from about 1 mm to about 30 mm. For example, the subassembly may have a length of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm.

The barbed rod assembly 220 may also include a termination subassembly 252 (i.e., an end subassembly) at an end of the barbed rod assembly 220. A termination subassembly 252 is similar to a subassembly 222; however, the termination subassembly 252 does not include a linking rod 240 because the termination subassembly 252 is designed to be coupled to the end of the barbed rod assembly 220.

The receiver 230, as shown in FIGS. 5A to 5D, of a subassembly 222 is configured to accept or receive the locking end of the linking rod 240 of a second subassembly 222 to couple the first subassembly 222 with the second subassembly 222. The receiver 230 includes a central opening 231 at the receiving end of the subassembly 222, whereby the central opening 231 is configured to receive the locking end of the linking rod 240 of a second subassembly 222. In one example, the central opening 231 may be cylindrically shaped, comprising a cylindrical void along the centerline axis of the receiver 230. In other examples, the central opening may include a cross section that is shaped to match the cross-section of the linking rod, including generally circular, elliptical, square, rectangular, or ovular. In one example, the central opening 231 may include an include an upper structure 234 projecting radially inward from the interior cylindrical surface of the central opening 231 of the receiver 230 and a lower structure 232 projecting radially inward from the interior cylindrical surface of the central opening 231 of the receiver 230. The back surfaces of the upper structure 234 and lower structure 232 may coincide with the back outer surface 236 that constitutes the back of the receiver 230. The upper structure 234 and lower structure 232 may define an aperture that extends through the centerline axis of the receiver 230. In other examples, the upper structure and lower structure may be created by subtraction from the interior cylindrical surface of the receiver, whereby material is removed from the interior receiver body to create surfaces for locking or coupling subassemblies together.

A receiver extension 238 extends around a central opening 231 of the receiver 230 to accommodate receipt of the locking end of a second subassembly 222 during coupling. In one example, the receiver extension 238 may include two receiver arms that extend laterally outward along the centerline axis of the receiver 230. In other examples, the receiver extension may include more than two arms. In other examples, the receiver extension may be configured in a variety of shapes—including in the shape of a sphere, cone, cylinder, pyramid, cube, cuboid, triangular prism, v-shape, or u-shape—to accommodate the receipt of the locking end of a second subassembly during coupling.

The locking end of the linking rod 240, as shown in FIGS. 6A to 6D, is configured to engage the receiver 230 of a second subassembly 222 to couple the first subassembly 222 with the second subassembly 222. The locking end of the linking rod 240 may contain a first structure 242 that extends radially outward from the linking rod 240 and creates a first locking surface 244. The locking end of the linking rod 240 may also contain a second structure 246 that projects radially outward from the linking rod 240 and creates a second locking surface 248. In other examples, the first locking surface and the second locking surface may be created by subtraction from the linking rod, whereby material is removed from the locking end of the linking rod to create the locking surfaces.

To couple two subassemblies 222 together, the locking end of the linking rod 240 of a first subassembly 222 may be inserted or transfixed into the central opening 231 of the receiver 230 of a second subassembly 222. The second structure 246 and second locking surface 248 of the linking rod 240 of a first subassembly 222 are inserted beyond the upper structure 234 and lower structure 232 of the receiver 230 of a second subassembly 222. The interior surfaces of the receiver extension 238 that face the central opening 231 of the second subassembly 222 may provide an alignment "stop," whereby the outer surface of the locking end of the linking rod 240 comes into contact with the interior surfaces of the receiver extension 238 at a depth of insertion that aligns the twist and lock mechanisms of the subassemblies 222. The first subassembly 222 and second subassembly 222 are twisted or rotated 90-degrees, with respect to each other, along the centerline axes of the receivers 230 and linking rods 240 of each subassembly 222. The 90-degree rotation will position the first locking surface 244 of the first structure 242 of the locking end of the linking rod 240 of the first subassembly 222 against the front-facing surfaces of the upper structure 234 and lower structure 232 in the receiver 230 of the second subassembly 222. Additionally, the 90-degree rotation will position the second locking surface 248 of the second structure 246 of the locking end of the linking rod 240 of the first subassembly 222 against the back-facing surfaces of the upper structure 234 and lower structure 232 in the receiver 230 of the second subassembly 222. This insert and twist or rotate procedure will couple or "lock" the subassemblies 222 together.

Figure 7A:
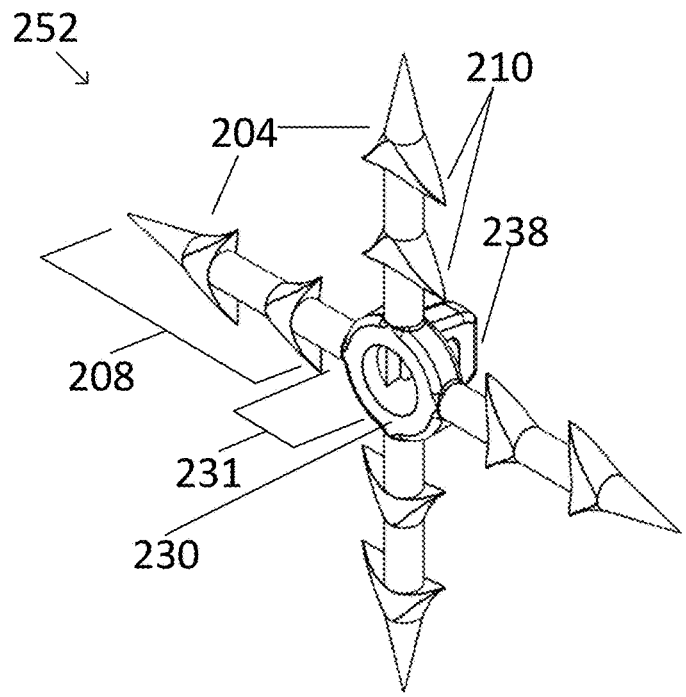
FIG. 7A is an isometric view of a termination subassembly.
Figure 7B:
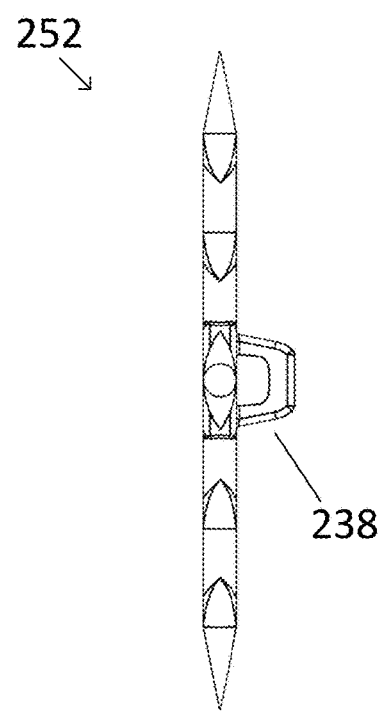
FIG. 7B is a sideview of a termination subassembly.
Figure 7C:
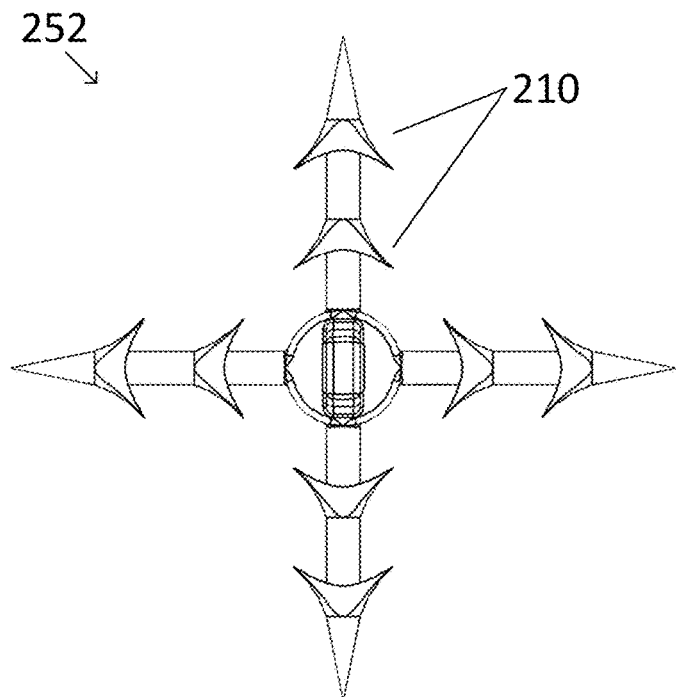
FIG. 7C is a back view of a termination subassembly.

Alternatively, instead of coupling two subassemblies 222 as described above, a first subassembly 222 can be coupled with a termination subassembly 252 at the end of a barbed rod assembly 220. As shown in FIGS. 7A to 7C, a termination subassembly 222 contains a plurality of barbs 204 extending outward from a receiver 230 and a receiver extension 238 extending around a central opening 231 of the receiver 230 along the centerline axis of the receiver 230. Recall that a termination subassembly 252 is similar to a subassembly 222 except the termination subassembly 252 does not include a linking rod 240. To couple the first subassembly 222 with a termination subassembly 252, the locking end of the linking rod 240 of a first subassembly 222 would be inserted into the central opening 231 of the receiver 230 of a termination subassembly 252. The 90-degree rotation described above would be employed to couple the first subassembly 222 with the termination subassembly 252.

The barbed rod assembly 220 may be used to close separated tissue. For example, the barbed rod assembly 220 may be placed inside open tissue such that the barbs 204 make contact with tissue. In some examples, the tissue may then be pressed against the barbs 204 such that the barbs penetrate and self-adhere to the tissue. In some examples, the barbed rod assembly 220 may be pressed into the tissue such that the barbs penetrate and self-adhere to the tissue.

The barbed rod assembly may be biologically resorbable with varying tensile strength and elasticity/rigidity characteristics for various applications. In at least one example, the barbed rod assembly is biodegradeable. The barbed rod assembly may be made of polyglactin, polydioxanone, polygelcaprone, poly-hydroxy-butyrate, calcium compounds (e.g., calcium sulfate, calcium hydroxyapatite, or other calcium compounds), or other resorbable materials. In some instances, parts or all of the barbed rod assembly may also be coated with metals, such as magnesium, titanium, nitinol, steel, and/or other biologically resorbable metals, to impart rigidity, tissue penetration, handling characteristics, texturing, friction, or to supplement the joining or locking mechanism to couple the receiver and linking rods in this modular embodiment of the device. Use of metals may also allow the barb to be bent or deformed into another angle or configuration. In one example, nitinol is used to allow the device to recoil to its original shape after the device is deformed. In some aspects, the biodegradable barbed rod assembly may last less than two weeks, two weeks, one year, or longer, or any other duration before being resorbed. In another example, the barbed rod assembly is permanent, i.e., not biodegradable. In such examples, the permanent barbed rod assembly may be made of polypropylene, nylon, or another non-biodegradable material. In yet another example, the linking rods are biodegradable and the barbs are permanent. In still another example, the linking rods are permanent and the barbs are biodegradable. In some embodiments, materials such as antibiotics or other drugs may be impregnated into the device.

Attached or connected to the receiver 230 are a plurality of rigid or semi-rigid barbs 204 that penetrate and self-adhere to tissue. The barbs may be straight, or they may bend or have sharp angles along the barb body. The barbs 204 may be placed in groups around the receiver 230 or could be placed individually on the receiver 230. For example, a group of barbs 204 may include 2, 3, 4, 5, or 6 barbs. In one example, each group of barbs alternates direction along the barbed rod assembly 220, i.e. one group oriented horizontally and the next group oriented vertically. The group of barbs 204 may be evenly spaced, circumferentially, around the receiver 230, spaced in a pattern, or could be randomly spaced. In at least one example, a group of barbs 204 includes 4 barbs extending radially out from the receiver 230 and spaced 90° from each other around the receiver 230. The length of the linking rod 240 and receiver extension 238 may be configured to provide a set distance of spacing between a first group of barbs 204 on a first subassembly 222 and a second group of barbs 204 on a second subassembly 222. The set distance may be about 1-20 mm. For example, a first group of barbs may be spaced 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm from a second group. The barbs 204 may extend from the receiver 230 at an angle relative to the centerline axis of the receiver 230 of less than or equal to 90 degrees. For instance, the barbs 204 may extend from the centerline axis of the receiver 230 at an angle of about 30°, 35°, 40°, 45°, 50°, 55°, 60°, 65°, 70°, 75°, 80°, 85°, or 90°.

The barbed rod assembly may be modular in multiple aspects. In one aspect, the modular barbs may come in a set, wherein the set of barbs may be fixed at any point along the linking rod. In one example, the set of barbs has a central opening that may be transfixed by the rod. In another example, the set of barbs has a central aperture that may be opened and placed along the rod at a given location, and then the aperture may be reversibly or irreversibly closed around the rod by a mechanical recoil, a snapping mechanism, peg system, threads and screws, or another joining mechanism. In another aspect, the modular rod may have a plurality of openings operable to receive the barbs. In one example, the barbs lock into the plurality of openings by a mechanical recoil, a snapping mechanism, a peg system, threads and screws, or another joining mechanism. In some examples, the barbs may be attached to the rod at an angle. In some examples, the joining mechanism may comprise a nonresorbable material to better facilitate joining the barbs to the rod and provide structural stability. The barbs may be manufactured separately from the rest of the device. Some methods for manufacturing the barbs may include injection molding. In some examples, the barbs may be manufactured and then later joined to the rod via an injection mold while keeping the barbs positionally stable, an adhesive, or other methods of attachment.

The barbs 204 may include a barb body 208, one or more projections 210 or smaller sub-barbs emanating from the barb body 208, and a tapered portion 206 ending at a point that is sufficient to pierce tissue. Projections 210 may extend from the barb body, from the tapered portion, or both. In some embodiments, each end of the barbed rod assembly 220 may also comprise a plurality of projections. In some embodiments, the tapered portion 206 may be replaced with a flat or blunted portion depending on the application and need. For instance, a barb blunted portion may be used to provide stability for the device. In some examples, the projections 210 may allow for the barb to be securely fixated in the tissues and provide resistance to pull out the barb from the penetrated tissues. The barbs 204 may be used in various quantities and concentrations within the barbed rod assembly 220. In some embodiments, the barbs are placed asymmetrically in relation to a cross-sectional perspective of the barbed rod assembly 220.

The barbs and projections may vary in type, quantity, thickness, length, angle, shape, spacing, or direction with various projection configurations. For example, the barbs may be round, triangular, or rectangular/prism-shaped, blade-like, curved, tooth-like, or may assume other similar forms. For example, the barbs may have a shape that allows tissue to be penetrated but not severed. The barbs may have a shape to optimize the stability of the barbs. For instance, the barbs may be wider at their base where they project from the rod and taper to a smaller diameter at the point of the barb to facilitate tissue penetration. The projections may be angled toward the rod to facilitate the barb's self-adherence to the tissue.

The barbs may have a length ranging from about 0.25-100 mm. In some examples, the barbs have a length of about 0.25-10 mm, 10-20 mm, 20-30 mm, 30-40 mm, 40-50 mm, 50-60 mm, 60-70 mm, 70-80 mm, 80-90 mm, or 90-100 mm. The barbs may have a diameter ranging from 0.25-15 mm. In some examples, the barbs have a diameter of 0.25-1 mm, 1-2 mm, 2-3 mm, 3-4 mm, 4-5 mm, 5-6 mm, 6-7 mm, 7-8 mm, 8-9 mm, 9-10 mm, 10-11 mm, 11-12 mm, 12-13 mm, 13-14 mm, or 14-15 mm. In some embodiments, the barbs have a length of about 3-4 mm and a diameter of about 0.7-1 mm. In other embodiments, the barbs have a length ranging from 0.25-20 mm. The barbs may have variable lengths and diameters depending on the application for the barbed rod assembly. The operator may choose the appropriate length and diameter based on the particular patient and situation at hand. For example, closing the skin and subcutaneous fat of a patient with a BMI of 25 would require shorter length barbs, while a patient with a BMI of 40 may require longer length barbs. Considerations for choosing the dimensions of the barbs include the thickness of the skin or subcutaneous tissues in the area of the body where the device is to be used.

The projections may extend radially from each barb. In some examples, the projections may extend at an angle from the barb body. Each of the plurality of projections may extend at an angle of less than or equal to 90 degrees from the barb body. For example, the projection may extend from the barb body at an angle of 15°, 20°, 25°, 30°, 35°, 40°, 45°, 50°, 55°, 60°, 65°, 70°, 75°, 80°, 85°, or 90°. The projections may have a tip that points towards the receiver or away from the receiver. In one embodiment, the projections are angled at 45 degrees toward the receiver in relation to the barb body. This may result in projections on different barbs pointing in different directions. For example, the tips of the projections on the barbs may all point towards the receiver, such that barbs that are on opposite sides of the receiver have projections that are pointing in opposite directions.

The projections may be macroscopic, shaped projections, or may be a textured surface added to the barb body by, for example, cutting or coating with another material that serves to generate resistance to pull-out. In some examples, the projections may be about 0.25 mm to about 10 mm in length. In some examples, the length of the projections may be about 0.25-1 mm, 1-2 mm, 2-3 mm, 3-4 mm, 4-5 mm, 5-6 mm, 6-7 mm, 7-8 mm, 8-9 mm, or 9-10 mm. In at least one example, the projections may be less than 1 mm in length. In some examples, the barb projections may be cut into the material of the barb body. In additional examples, the barb projections may be fabricated by, for example, an injection mold technique, 3D printing, stereolithography, or laser-cutting. The projections may be created by the same methods as the barb body, by subtraction or precipitation, or by coating with a material generating a roughened surface. The projections may be macroscopic, shaped projections, or may be a textured surface added to the barbs by, for example, cutting, rasping, or coating (with another material) which serves to generate resistance to pull-out as the macroscopic projections would.

Figure 8A:
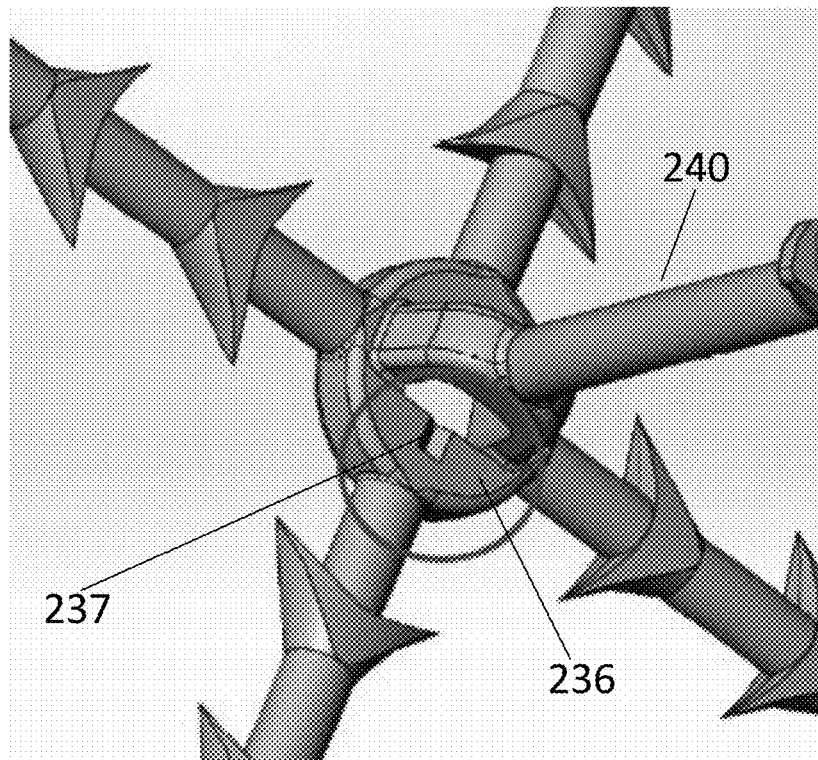
FIG. 8A is a perspective view detailing a locking feature integrated into the back surface of the receiver.
Figure 8B:
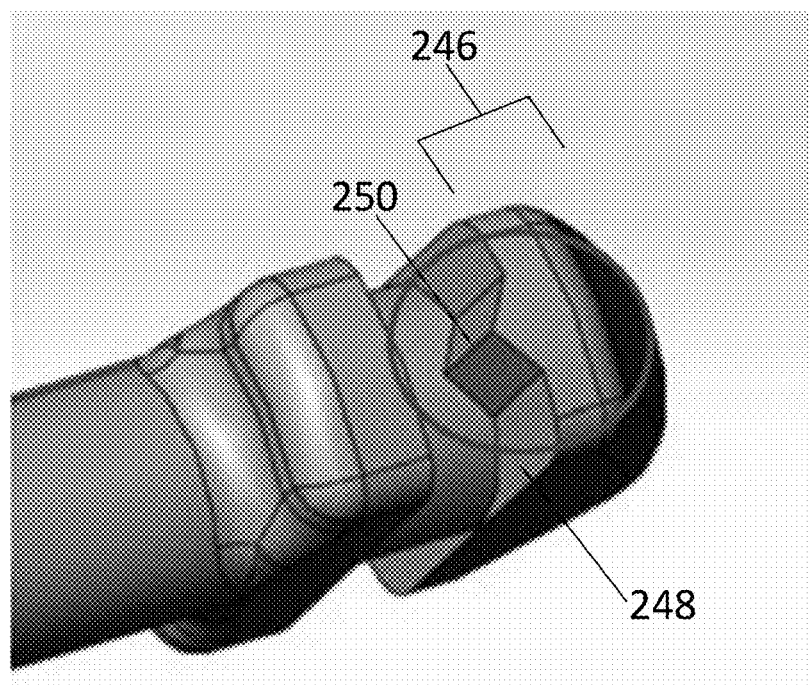
FIG. 8B is a perspective view detailing an additional locking element integrated into the locking end of the linking rod.

In some embodiments, as shown in FIGS. 8A and 8B, the back outer surface 236 of the receiver 230 may contain at least one notch 237 in the back outer surface 236. In some embodiments, the notch may be placed into the back surface of either the upper structure or lower structure. The notch 237 may be configured to accept a corresponding boss 250, extending from the second locking surface 248 of the second structure 246 of the linking rod 240, in order to lock and align subassemblies 222 that have been coupled by inserting and then twisting or rotating two subassemblies 90-degrees. In a locked position, the boss 250 will be positioned within the notch 237 to inhibit inadvertent twisting, rotation, or otherwise unlocking of the subassemblies 222. The boss 250 can be configured in a variety of shapes—including in the shape of a sphere, cone, cylinder, pyramid, cube, cuboid, triangular prism, v-shape, or u-shape—and, correspondingly, the notch 237 can be configured in any corresponding shape to accept the boss 250. In other examples, a boss and corresponding notch may be configured on other elements of the subassembly to inhibit inadvertent twisting, rotation, or otherwise unlocking of the subassemblies. For example, the notch may be installed on the locking surface at the locking end of the linking rod and the boss may be installed on the back outer surface of the receiver.

Figure 9A:
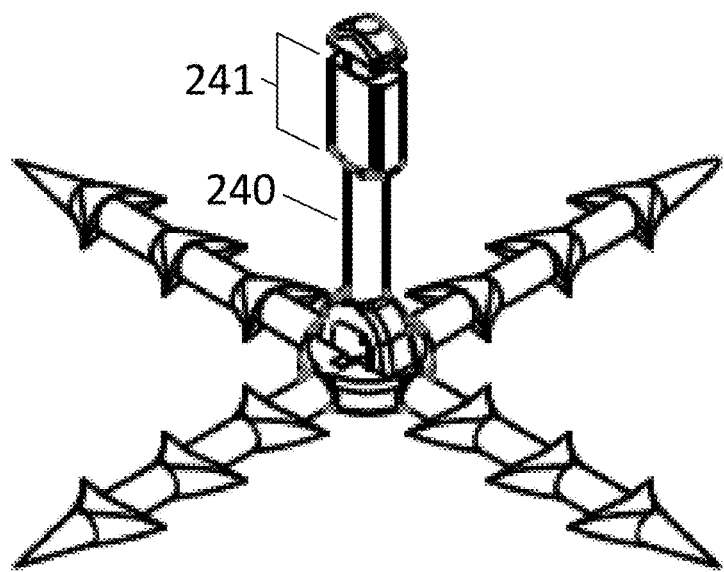
FIG. 9A is perspective view of a subassembly including an additional structure at the locking end of the linking rod.
Figure 9B:
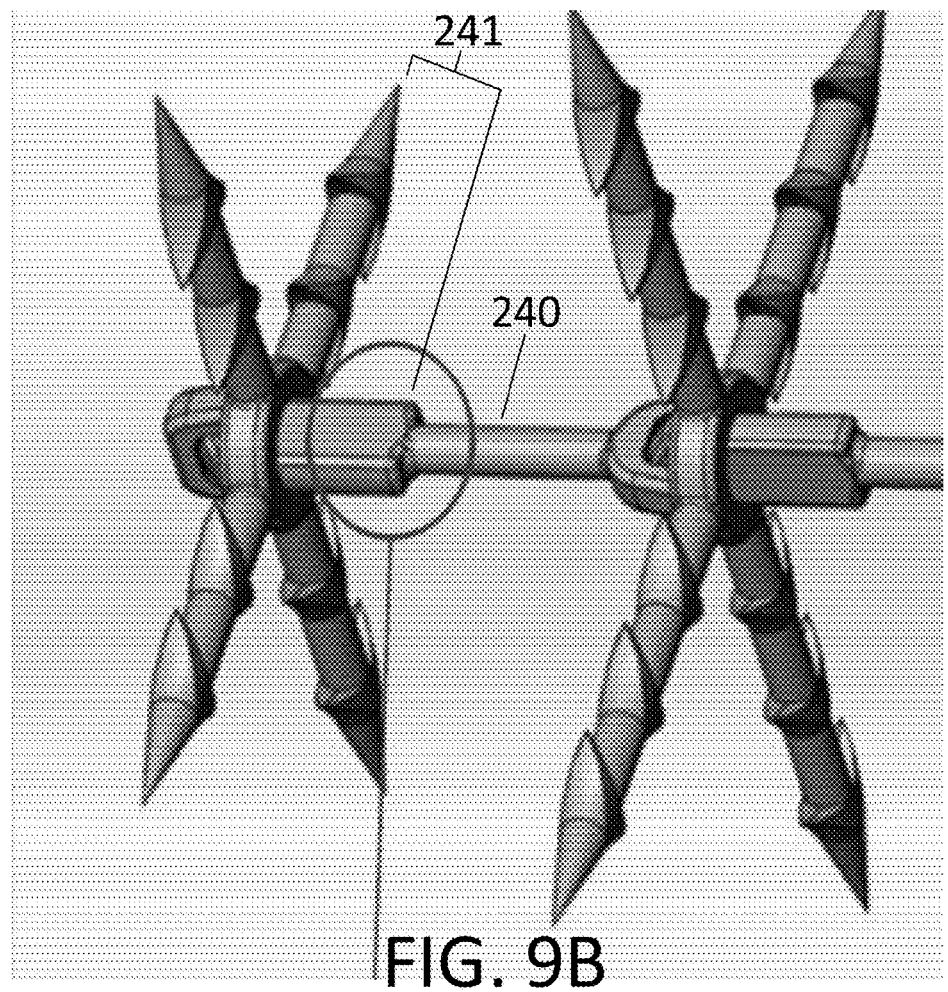
FIG. 9B is another perspective view of a subassembly including an additional structure at the locking end of the linking rod.
Figure 10:
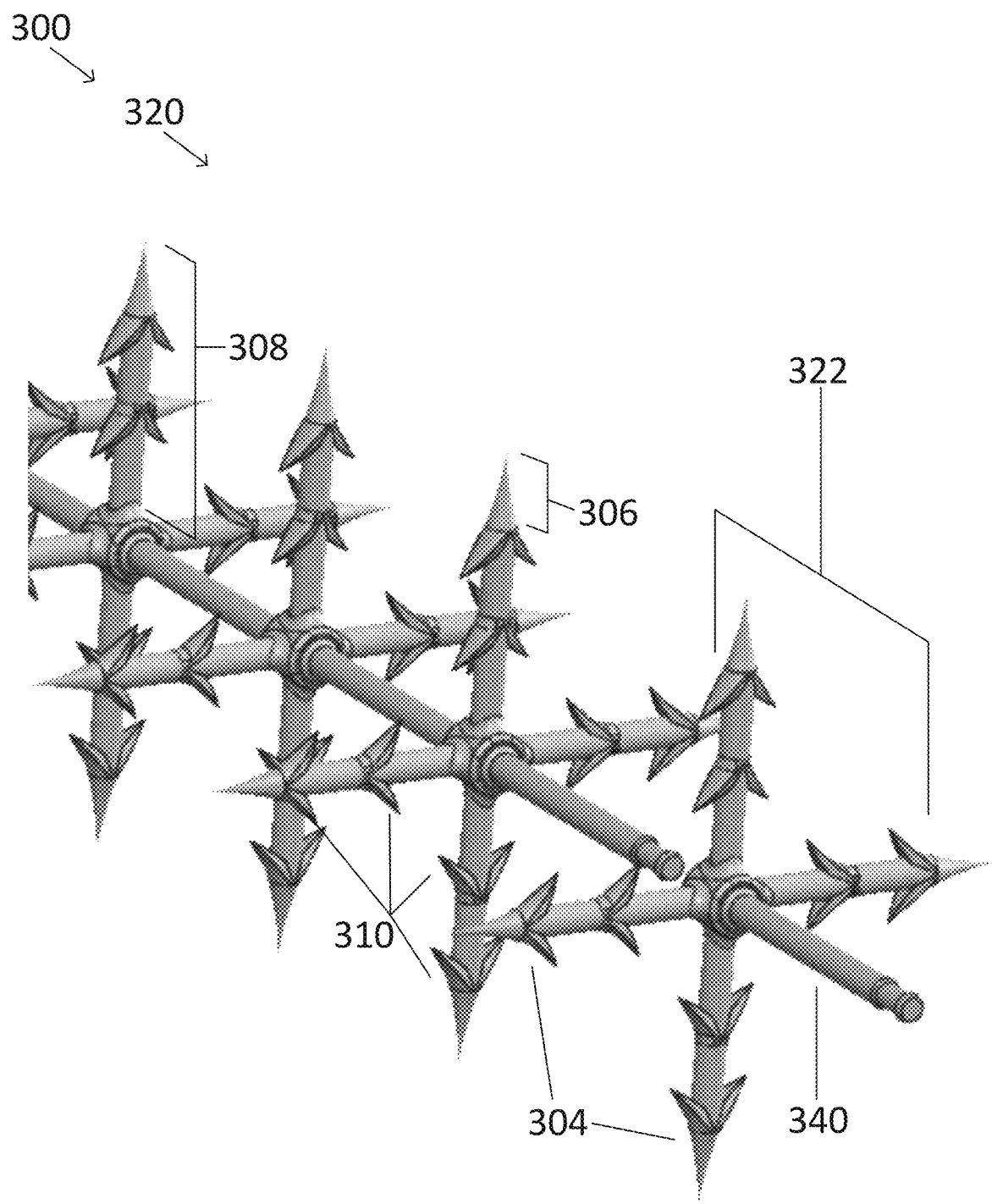
FIG. 10 is a perspective view of a barbed rod assembly for linear tissue closure including snap and lock coupling mechanisms.

In some embodiments, as shown in FIGS. 9A and 9B, the linking rod 240 may include a reinforcing bar 241 extending radially outwardly from the linking rod 240. The reinforcing bar 241 is designed to add material to the linking rod 240 to provide additional strength to withstand stress imparted on the linking rod 240 when a first subassembly 222 is rotated or twisted 90-degrees with respect to a second subassembly 222. In other words, the reinforcing bar 241 may prevent deformation or failure of the linking rod 240. In one example, the reinforcing bar 241 includes flat surfaces that may provide for easier griping at the end of the linking rod 240 during the assembly or coupling of subassemblies 222. The assembly may be performed by hand, by tool, or by a robot during automaton assembly. In other examples, the reinforcing bar may have a generally circular, elliptical, square, rectangular, or ovular cross-section. In an embodiment, the reinforcing bar 241 may extend radially outward near the receiver end of the linking rod 240. In another embodiment, the reinforcing bar 241 may extend radially outward near the locking end of the linking rod 240. The reinforcing bar 241 may be incorporated with the first structure 242 that extends radially outward from the linking rod 240, as shown in FIGS. 9A and 9B, In another embodiment, as shown in FIGS. 10 to 13C, the barbed rod 200 may be a modular barbed rod assembly 320. Sets of barb subassemblies 322 can be coupled together by snap and lock mechanisms incorporated into each subassembly 322 to form the modular barbed rod assembly 320. Referring to FIG. 10, each subassembly 322 contains a plurality of barbs 304 extending radially outward from a receiver 330 and a linking rod 340 comprising a receiver end and a locking end opposite the receiver end, wherein the linking rod 340 is connected to the receiver 330 at one end and extends laterally outward from the receiver 330 along the centerline axis of the receiver 330. The linking rod 340 may have a generally circular, elliptical, square, rectangular, or ovular cross-section. Each of the plurality of barbs 304 comprises a barb body 308, which includes a plurality of projections 310 placed along the barb body 308 and angled toward the receiver 330. In some embodiments, each of the plurality of barbs 304 includes a tapered end 306.

The subassemblies 322 may be provided in multiple sizes. In some examples, subassemblies 322 may be coupled together and packaged as barbed rod assemblies 320 of various lengths. In other examples, the barbed rod assemblies may contain additional modularity in that the linking rod may have openings in it operable to receive barbs. The barbs may then be mated to the openings in the linking rod. The diameter of the barbed rod assembly—as measured from the tip of one barb to the tip of a barb on the opposite side of the receiver—may range from about 1 mm to about 100 mm. For example, the barbed rod assembly may have a diameter of 1-5 mm, 5-10 mm, 10-15 mm, 15-20 mm, 20-25 mm, 25-30 mm, or 30-35 mm, 35-40 mm, 40-45 mm, 45-50 mm, 55-60 mm, 60-65 mm, 65-70 mm, 70-75 mm, 75-80 mm, 80-85 mm, 85-90 mm, 90-95 mm, or 95-100 mm. In other embodiments, the barbed rod assembly may have a diameter ranging from 1.5-100 mm. In one example, a small barbed rod assembly only 3-4 mm in diameter may be used to accommodate closure of thin tissues such as on the forearm or other areas where skin is thin. In another example, a larger barbed rod assembly 4-5 cm in diameter may be used to accommodate closure of thick tissues such as on the abdomen or other areas where skin is thick. The length of the subassembly 322 may range from about 1 mm to about 30 mm. For example, the subassembly may have a length of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm.

Figure 11A:
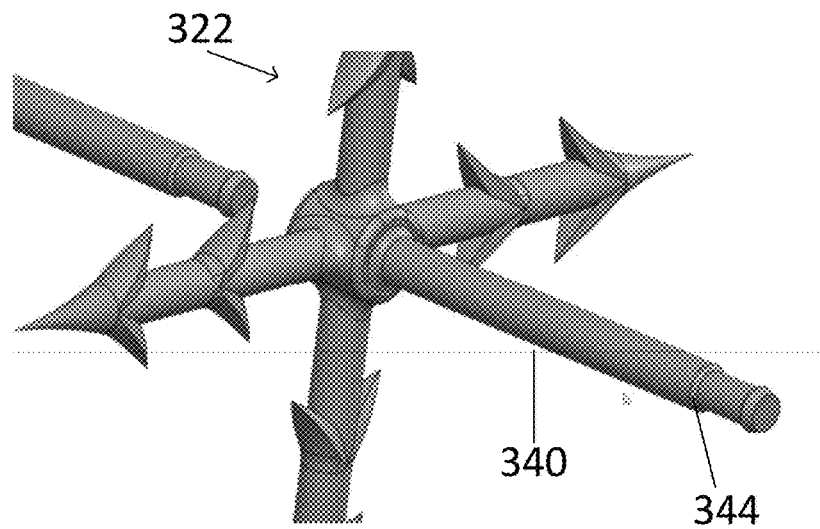
FIG. 11A is a perspective view of a subassembly with a snap and lock coupling mechanism.
Figure 11B:
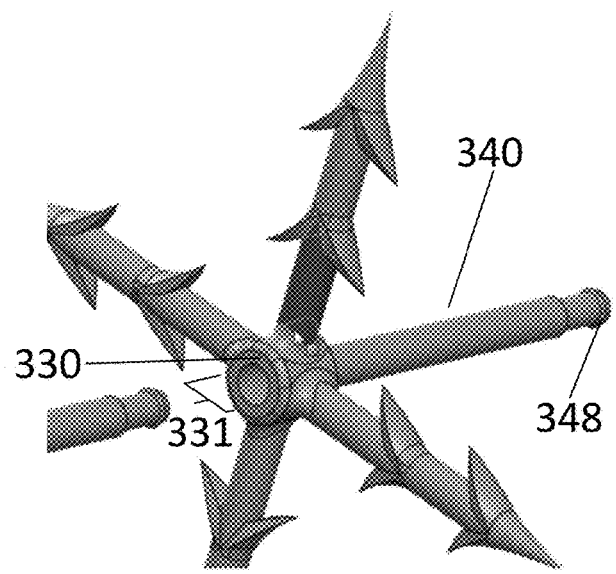
FIG. 11B is another perspective view of a subassembly with a snap and lock coupling mechanism.
Figure 11C:
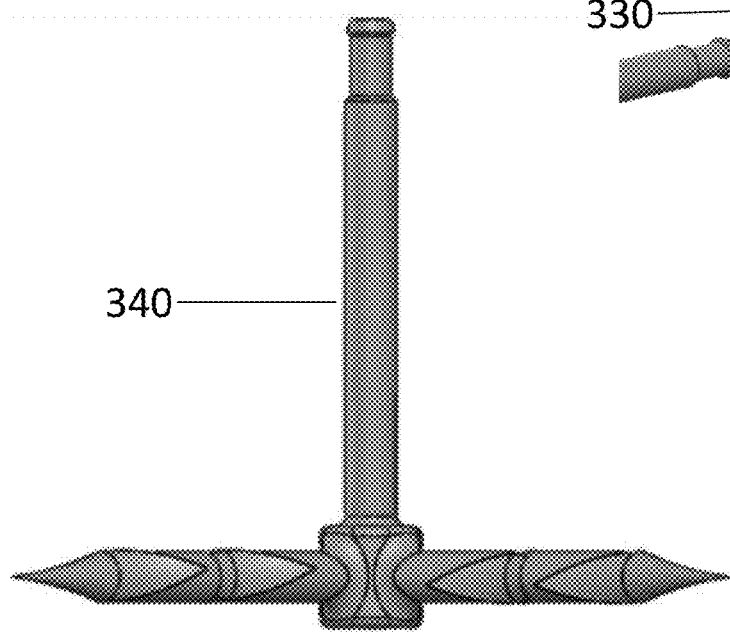
FIG. 11C is a top view of a subassembly with a snap and lock coupling mechanism.

The receiver 330, as shown in FIG. 11B, of a subassembly 322 is configured to accept or receive the locking end of the linking rod 340 of a second subassembly 322 to couple the first subassembly 322 with the second subassembly 322. The receiver 330 includes a central opening 331 at the receiver end of the subassembly 322, whereby the central opening 331 is configured to receive the locking end of the linking rod 340 of a second subassembly 322. In one example, the central opening 331 may be cylindrically shaped, comprising a cylindrical void along the central axis of the receiver 230. In other examples, the central opening may include a cross section that is shaped to match the cross-section of the linking rod, including generally circular, elliptical, square, rectangular, or ovular. The cylindrical interior surface of the central opening 331 may contain an internal structure 334 projecting radially inward to define locking surfaces. In other examples, the internal structure may be created by subtraction from the interior cylindrical surface of the receiver, whereby material is removed from the interior receiver body to create surfaces for locking or coupling subassemblies together.

Figure 12A:
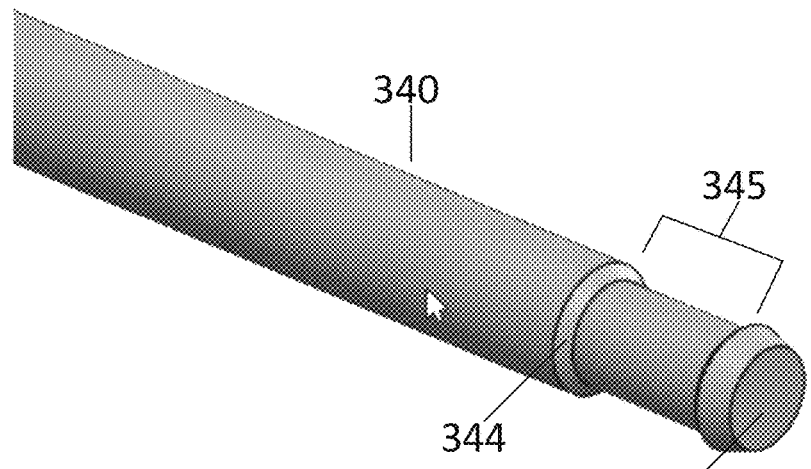
FIG. 12A is a perspective view of the locking end of the linking rod of a subassembly with a snap and lock coupling mechanism.
Figure 12B:
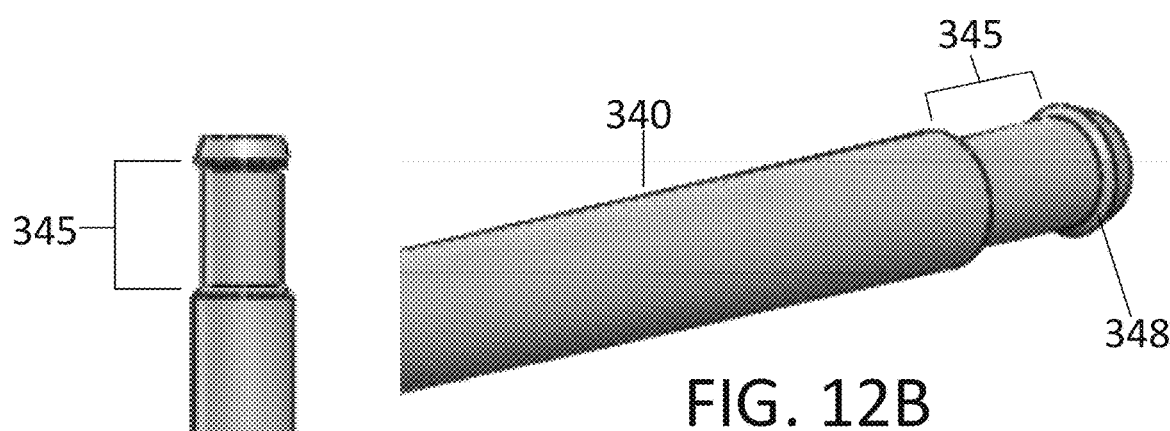
FIG. 12B is another perspective view of the locking end of the linking rod of a subassembly with a snap and lock coupling mechanism.
Figure 12C:
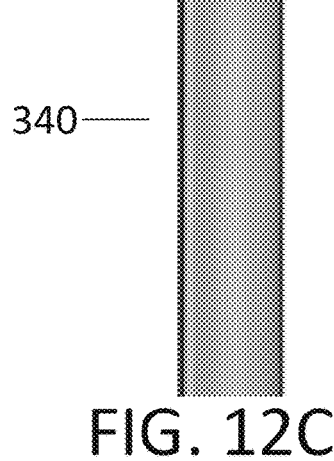
FIG. 12C is a top view of the lokcing end of the linking rod of a subassembly with a snap and lock coupling mechanism.

The locking end of the linking rod 340, as shown in FIGS. 12A to 12C, is configured to engage the receiver 330 of a second subassembly 322 to couple the first subassembly 322 with the second subassembly 322. In one example, the locking end of the linking rod 340 may contain a recess 345 oriented radially around the circumference of the locking end of the linking rod 340. The recess 345 may define a first locking surface 344 and a second locking surface 348. In other examples, the locking surfaces may be created by adding structures extending radially outward from the linking rod, whereby material is added to the locking end of the linking rod to create the locking surfaces. The first locking surface 344 and the second locking surface 348 may be perpendicular with respect to the outer surface of the linking rod 340 or the surfaces may be angled or tapered. The locking end of the linking rod 340 terminates at an outer surface 349.

To couple two subassemblies 322 together, the locking end of the linking rod 340 of a first subassembly 322 may be inserted or transfixed into the central opening 331 of the receiver 330 of a second subassembly 322, as shown in FIGS. 13A to 13C. During the process of inserting the first subassembly 322 into the second subassembly 322, the subassemblies 322 will eventually "snap" together—the second locking surface 348 of the locking end of the linking rod 340 of the first subassembly 322 is inserted beyond the internal structure 334 within the central opening 331 of the receiver 330 of the second subassembly 322.

At the depth of full insertion, the two subassemblies 322 will be couped together by a friction fit. When coupled, the outer surface 349 of the linking rod 340 of a first subassembly 322 is positioned against the interior surface of the central opening 331 of the receiver 330 of the second subassembly 322. Simultaneously, the second locking surface 348 of the linking rod 340 of the first subassembly 322 will be positioned against a surface of the internal structure 334 in the central opening 331 of the receiver 330 of the second subassembly 322. This insert and snap procedure will couple or "lock" the subassemblies 322 together. In other examples, the locking end of the linking rod and the interior surfaces of the receiver may include combinations of structures and/or subtractions that allow the linking bar of a first subassembly and receiver of a second subassembly to snap together.

Alternatively, instead of coupling two subassemblies as described above, a first subassembly can be coupled with a termination subassembly at the end of a barbed rod assembly. A termination subassembly contains a plurality of barbs extending outward from a receiver. The termination subassembly is similar to a subassembly except the termination subassembly does not include a linking rod. To couple the first subassembly with a termination subassembly, the linking end of the linking rod of a first subassembly would be inserted into the central opening of the receiver of a termination subassembly. The snapping procedure described above would be employed to couple the first subassembly with the termination subassembly.

The barbed rod assembly 320 may be used to close separated tissue. For example, the barbed rod assembly 320 may be placed inside open tissue such that the barbs 304 make contact with tissue. In some examples, the tissue may then be pressed against the barbs 304 such that the barbs penetrate and self-adhere to the tissue. In some examples, the barbed rod assembly 320 may be pressed into the tissue such that the barbs penetrate and self-adhere to the tissue.

The barbed rod assembly may be biologically resorbable with varying tensile strength and elasticity/rigidity characteristics for various applications. In at least one example, the barbed rod assembly is biodegradeable. The barbed rod assembly may be made of polyglactin, polydioxanone, poly-gelcaprone, poly-hydroxy-butyrate, calcium compounds (e.g., calcium sulfate, calcium hydroxyapatite, or other calcium compounds), or other resorbable materials. In some instances, parts or all of the barbed rod assembly may also be coated with metals, such as magnesium, titanium, nitinol, steel, and/or other biologically resorbable metals, to impart rigidity, tissue penetration, handling characteristics, texturing, friction, or to supplement the joining or locking mechanism to couple the receiver and linking rods in this modular embodiment of the device. Use of metals may also allow the barb to be bent or deformed into another angle or configuration. In one example, nitinol is used to allow the device to recoil to its original shape after the device is deformed. In some aspects, the biodegradable barbed rod assembly may last less than two weeks, two weeks, one year, or longer, or any other duration before being resorbed. In another example, the barbed rod assembly is permanent, i.e., not biodegradable. In such examples, the permanent barbed rod assembly may be made of polypropylene, nylon, or another non-biodegradable material. In yet another example, the linking rods are biodegradable and the barbs are permanent. In still another example, the linking rods are permanent and the barbs are biodegradable. In some embodiments, materials such as antibiotics or other drugs may be impregnated into the device.

Attached or connected to the receiver 330 are a plurality of rigid or semi-rigid barbs 304 that penetrate and self-adhere to tissue. The barbs may be straight, or they may bend or have sharp angles along the barb body. The barbs 304 may be placed in groups around the receiver 330 or could be placed individually on the receiver 330. For example, a group of barbs 304 may include 2, 3, 4, 5, or 6 barbs. In one example, each group of barbs alternates direction along the barbed rod assembly 320, i.e. one group oriented horizontally and the next group oriented vertically. The group of barbs 304 may be evenly spaced, circumferentially, around the receiver 330, spaced in a pattern, or could be randomly spaced. In at least one example, a group of barbs 304 includes 4 barbs extending radially out from the receiver 330 and spaced 90° from each other around the receiver 330. The length of the linking rod 340 may be configured to provide a set distance of spacing between a first group of barbs 304 on a first subassembly 322 and a second group of barbs 304 on a second subassembly 322. The set distance may be about 1-20 mm. For example, a first set of barbs may be spaced 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm from a second group. The barbs 304 may extend from the receiver 330 at an angle relative to the centerline axis of the receiver 330 of less than or equal to 90 degrees. For instance, the barbs 304 may extend from the centerline axis of the receiver 330 at an angle of about 30°, 35°, 40°, 45°, 50°, 55°, 60°, 65°, 70°, 75°, 80°, 85°, or 90°.

The barbed rod assembly may be modular in multiple aspects. In one aspect, the modular barbs may come in a set, wherein the set of barbs may be fixed at any point along the linking rod. In one example, the set of barbs has a central opening that may be transfixed by the rod. In another example, the set of barbs has a central aperture that may be opened and placed along the rod at a given location, and then the aperture may be reversibly or irreversibly closed around the rod by a mechanical recoil, a snapping mechanism, peg system, threads and screws, or another joining mechanism. In another aspect, the modular rod may have a plurality of openings operable to receive the barbs. In one example, the barbs lock into the plurality of openings by a mechanical recoil, a snapping mechanism, a peg system, threads and screws, or another joining mechanism. In some examples, the barbs may be attached to the rod at an angle. In some examples, the joining mechanism may comprise a nonresorbable material to better facilitate joining the barbs to the rod and provide structural stability. The barbs may be manufactured separately from the rest of the device. Some methods for manufacturing the barbs may include injection molding. In some examples, the barbs may be manufactured and then later joined to the rod via an injection mold while keeping the barbs positionally stable, an adhesive, or other methods of attachment.

The barbs 304 may include a barb body 308, one or more projections 310 or smaller sub-barbs emanating from the barb body 308, and a tapered portion 306 ending at a point that is sufficient to pierce tissue. Projections 310 may extend from the barb body, from the tapered portion, or both. In some embodiments, each end of the barbed rod assembly 320 may also comprise a plurality of projections. In some embodiments, the tapered portion 306 may be replaced with a flat or blunted portion depending on the application and need. For instance, a barb blunted portion may be used to provide stability for the device. In some examples, the projections 310 may allow for the barb to be securely fixated in the tissues and provide resistance to pull out the barb from the penetrated tissues. The barbs 304 may be used in various quantities and concentrations within the barbed rod assembly 320. In some embodiments, the barbs are placed asymmetrically in relation to a cross-sectional perspective of the barbed rod assembly 320.

The barbs and projections may vary in type, quantity, thickness, length, angle, shape, spacing, or direction with various projection configurations. For example, the barbs may be round, triangular, or rectangular/prism-shaped, blade-like, curved, tooth-like, or may assume other similar forms. For example, the barbs may have a shape that allows tissue to be penetrated but not severed. The barbs may have a shape to optimize the stability of the barbs. For instance, the barbs may be wider at their base where they project from the rod and taper to a smaller diameter at the point of the barb to facilitate tissue penetration. The projections may be angled toward the rod to facilitate the barb's self-adherence to the tissue.

The barbs may have a length ranging from about 0.25-100 mm. In some examples, the barbs have a length of about 0.25-10 mm, 10-20 mm, 20-30 mm, 30-40 mm, 40-50 mm, 50-60 mm, 60-70 mm, 70-80 mm, 80-90 mm, or 90-100 mm. The barbs may have a diameter ranging from 0.25-15 mm. In some examples, the barbs have a diameter of 0.25-1 mm, 1-2 mm, 2-3 mm, 3-4 mm, 4-5 mm, 5-6 mm, 6-7 mm, 7-8 mm, 8-9 mm, 9-10 mm, 10-11 mm, 11-12 mm, 12-13 mm, 13-14 mm, or 14-15 mm. In some embodiments, the barbs have a length of about 3-4 mm and a diameter of about 0.7-1 mm. In other embodiments, the barbs have a length ranging from 0.25-20 mm. The barbs may have variable lengths and diameters depending on the application for the barbed rod assembly. The operator may choose the appropriate length and diameter based on the particular patient and situation at hand. For example, closing the skin and subcutaneous fat of a patient with a BMI of 25 would require shorter length barbs, while a patient with a BMI of 40 may require longer length barbs. Considerations for choosing the dimensions of the barbs include the thickness of the skin or subcutaneous tissues in the area of the body where the device is to be used.

The projections may extend radially from each barb. In some examples, the projections may extend at an angle from the barb body. Each of the plurality of projections may extend at an angle of less than or equal to 90 degrees from the barb body. For example, the projection may extend from the barb body at an angle of 15°, 20°, 25°, 30°, 35°, 40°, 45°, 50°, 55°, 60°, 65°, 70°, 75°, 80°, 85°, or 90°. The projections may have a tip that points towards the receiver or away from the receiver. In one embodiment, the projections are angled at 45 degrees toward the receiver in relation to the barb body. This may result in projections on different barbs pointing in different directions. For example, the tips of the projections on the barbs may all point towards the receiver, such that barbs that are on opposite sides of the receiver have projections that are pointing in opposite directions.

The projections may be macroscopic, shaped projections, or may be a textured surface added to the barb body by, for example, cutting or coating with another material that serves to generate resistance to pull-out. In some examples, the projections may be about 0.25 mm to about 10 mm in length. In some examples, the length of the projections may be about 0.25-1 mm, 1-2 mm, 2-3 mm, 3-4 mm, 4-5 mm, 5-6 mm, 6-7 mm, 7-8 mm, 8-9 mm, or 9-10 mm. In at least one example, the projections may be less than 1 mm in length. In some examples, the barb projections may be cut into the material of the barb body. In additional examples, the barb projections may be fabricated by, for example, an injection mold technique, 3D printing, stereolithography, or laser-cutting. The projections may be created by the same methods as the barb body, by subtraction or precipitation, or by coating with a material generating a roughened surface. The projections may be macroscopic, shaped projections, or may be a textured surface added to the barbs by, for example, cutting, rasping, or coating (with another material) which serves to generate resistance to pull-out as the macroscopic projections would.

Figure 14A:
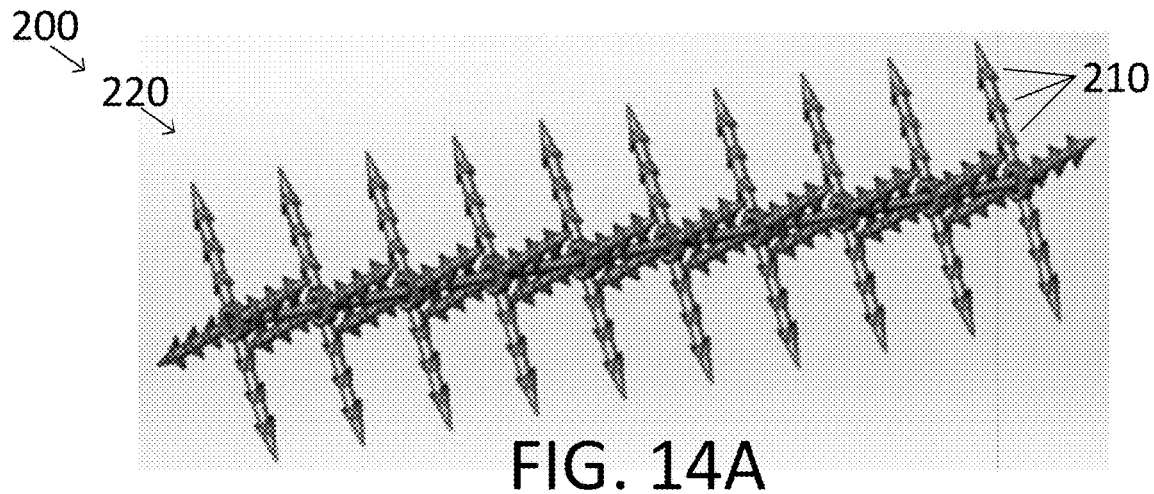
FIG. 14A is a perspective view of an example barbed rod assembly for linear tissue closure.
Figure 14B:
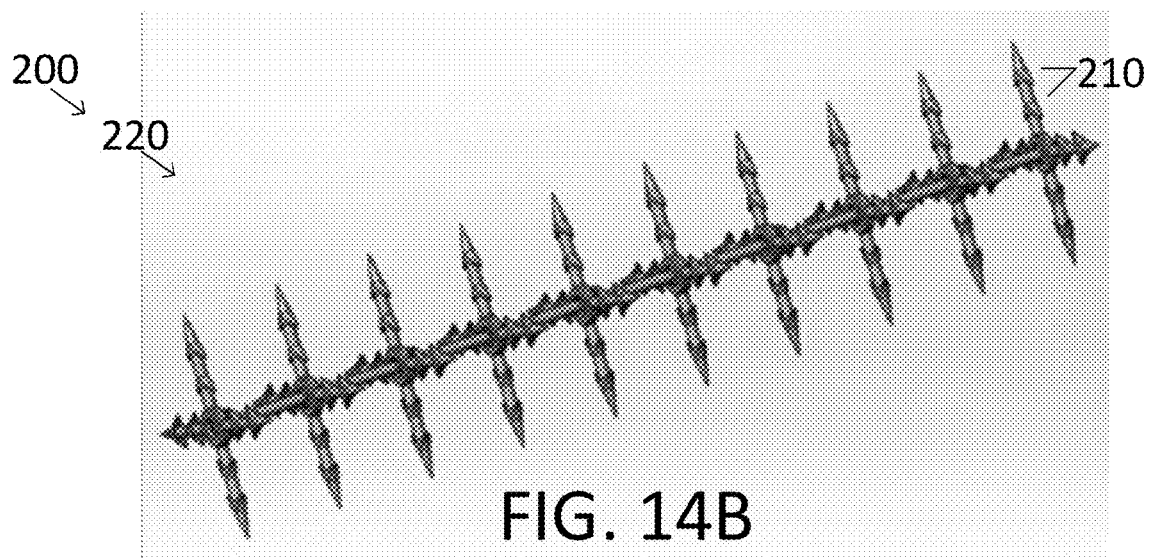
FIG. 14B is a perspective view of another example barbed rod assembly for linear tissue closure.
Figure 14C:
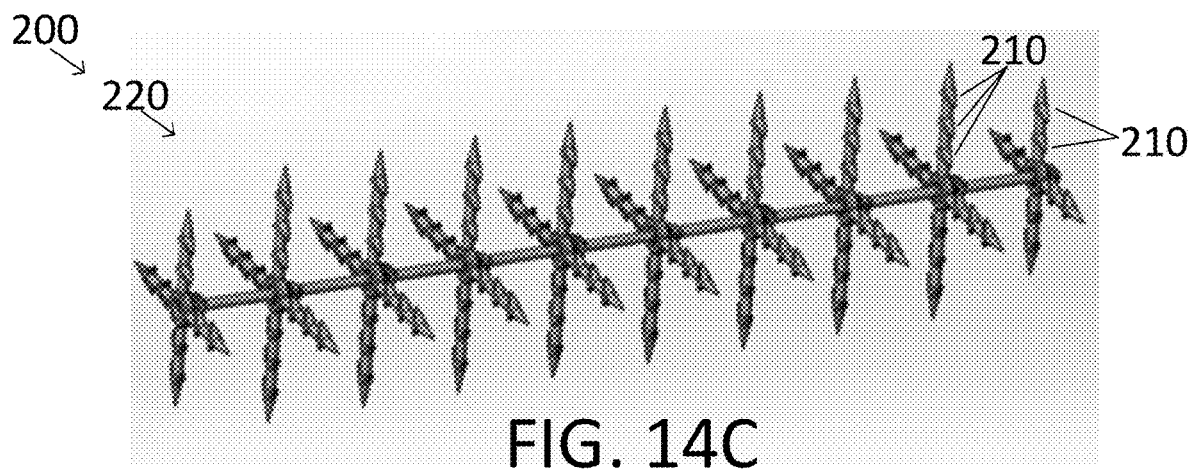
FIG. 14C is a perspective view of another example barbed rod assembly for linear tissue closure.

The barbed rod assemblies 220 may have various configurations of subassemblies 222, barbs 204, and projections 210. For example, FIG. 14A shows a barbed rod assembly 220 including ten subassemblies 222, in which each subassembly 222 contains four barbs 204 and each barb 204 includes three sets of projections 210 along the length of the barb bodies 208. FIG. 14B shows a barbed rod assembly 220 including ten subassemblies 222, in which each subassembly 222 contains four barbs 204 and each barb 204 includes two sets of projections 210 along the length of the barb bodies 208. FIG. 14C shows a barbed rod assembly 220 including ten subassemblies 222, in which each subassembly 222 contains four barbs 204. The barbs 204 at each end of the assembly 220 include two sets of projections 210 along the length of the barb bodies 208 and the middle eight subassemblies 222 contain three sets of projections 210 along the length of the barb bodies 208.

In at least one example, the device is biodegradable. The device may degrade after a period of time long enough for the tissue to have healed and the device is no longer needed for closure/repair. In some examples, the rod, barbs, and/or projections may be made of polyglactin, polydioxanone, polyglecaprone, polyhydroxybutyrate, calcium compounds (e.g., calcium sulfate, calcium hydroxyapatite, or other calcium compounds), magnesium, or other resorbable materials. In some examples, the rod, barbs, and projections are made of the same materials. In other examples, the rod, barbs, and projections are made of different materials.

The device may be operable to close tissue subcutaneously, transcutaneously, trans-fascially, trans-muscularly, across ligamentous tissue, across tendinous tissue, or across joint capular tissue. In a subcutaneous position, the device closes the subcutaneous tissue and may approximate the dermis, while the epidermis may be closed by using another method of superficial tissue closure, such as butterfly bandages, tissue adhesives, a zip surgical skin closure system, adhesive dressings, negative pressure systems, sutures, staples, or other methods. In a transcutaneous position, the device may provide final closure of the skin and other tissues. The device may approximate the tissues in other positions, such as trans-fascially, trans-muscularly, across ligamentous tissue, across tendinous tissue, or across joint capular tissue. The device likely is not suitable for retrorectus or intraperitoneal positioning. The barbs, the rod, or both, may be elastic or have other deformational characteristics that may allow the device to better align tissues in three dimensions.

In some instances, the level of approximation may vary depending on the cross-sectional diameter of the barbed rod device or the length of the barbs. As an example, a barbed rod device having a cross-sectional diameter of 3 cm is placed in a subcutaneous position where the combined thickness of the dermal and subcutaneous tissue is 3 cm, then it is possible that greater approximation or tighter tissue closure would occur near the center of the device, i.e., at 1.5 cm deep, where the barbs join the rod and are closer together. In the same example, looser or less stable approximation may occur at areas further from the center of the device. However, in these examples, the device is still expected to impart three-dimensional stability to all of the penetrated tissues.

Further provided herein are methods of skin or soft tissue closure or approximation using the barbed rod. Currently, suturing and stapling are the standards for closing skin or soft tissue incisions. An example would be a laparotomy incision, a midline sternal incision or an abdominoplasty incision. If an incision is long, this can be a time-consuming process. The ultimate quality of closure is dependent on the operator and can make a difference with regards to risks of complications. Deeper layers of tissue are not approximated with stapling and skin suturing, unless the operator makes a specific, additional effort to do so. The barbed rod may be used as a replacement for, or supplement to, sutures and staples. An entire incision, including the full thickness of the subcutaneous tissue, may be closed or approximated in a matter of seconds with application of one barbed rod. This would provide tissue immobilization for healing in a rapid but stable fashion. This would reduce the tendency towards shearing of tissue planes and dead space formation or accumulation of fluid within potential spaces.

A method of tissue closure may include placing the barbed rod inside the edges of an opened tissue (e.g. incision) and pressing the edges of the opened tissue into the barbed rod such that the barbs penetrate and are retained within the tissue. In some examples the method may include pressing the barbed rod into the edges of the opened tissue. In some aspects, this may be achieved by manipulating the tissues with a surgical instrument or with one's hands as the device is pressed into place. The device may be applied subcutaneously, transcutaneously, trans-fascially, trans-muscularly, across ligamentous tissue, across tendinous tissue, or across joint capular tissue. The barbed rod device may also be rotated along the axis of the rod as it is placed.

In one example, the device is placed in a subcutaneous position between two tissues, wherein the tissues on one side are in a higher position than those on the other side. The device then penetrates the tissue on the lower side of the incision and is rotated along the axis of the rod as it is brought to the other side of the incision to penetrate the tissues in the higher position. This may elevate the tissues that occupied a lower position before the device was placed.

In another example, the barbed rod device may be pressed downward into tissue below a wound or incision. This stabilizes the device such that overlying subcutaneous tissues may be fixed in a stable position. In some examples, to perform this method, the device may include barbs that are placed asymmetrically along the rod when viewed in a cross-sectional plane. For instance, a device may have a single barb pointing downward into the tissue below the wound or incision, and two sets of barbs may be pointing upward at a 90 degree angle relative to one another, such that the device forms a "Y" shape. In another example, a device has three barbs facing downward to provide stability and two barbs on the sides of the device to penetrate tissue on either side of the wound or incision.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

Numerous examples are provided herein to enhance the understanding of the present disclosure. A specific set of statements are provided as follows.

Statement 1. A device for tissue closure comprising two or more subassemblies, each subassembly comprising: a receiver having a central opening and centerline axis; a plurality of barbs extending radially outward from the receiver; and a linking rod extending from the receiver along the centerline axis of the receiver, the linking rod comprising a locking end opposite the receiver, wherein the locking end of a first subassembly is configured to engage the receiver of a second subassembly.

Statement 2. The device of Statement 1, wherein one of the subassemblies is an end subassembly that does not include the linking rod.

Statement 3. The device of Statement 1, wherein the locking end of the first subassembly and the receiver of the second subassembly comprise twist and lock mechanisms for coupling the subassemblies together.

Statement 4. The device of Statement 3, wherein the linking rod further comprises a reinforcing bar extending radially outward from the linking rod.

Statement 5. The device of Statement 1, wherein the locking end of the first subassembly and the receiver of the second subassembly comprise snap and lock mechanisms for coupling the subassemblies together.

Statement 6. The device of Statement 1, wherein each of the plurality of barbs further comprises a plurality of projections.

Statement 7. The device of Statement 6, wherein the length of each of the plurality of projections is 0.25-10 mm.

Statement 8. The device of Statement 6, wherein each of the plurality of projections extends at an angle of less than 90 degrees from the barb.

Statement 9. The device of Statement 7, wherein each of the plurality of projections extends at an angle of 45 degrees from the barb.

Statement 10. The device of Statement 7, wherein each of the plurality of projections is angled toward the receiver.

Statement 11. The device of Statement 1, wherein the device is operable to close tissue subcutaneously, trans-cutaneously, trans-fascially, trans-muscularly, across ligamentous tissue, across tendinous tissue, or across joint capular tissue.

Statement 12. The device of Statement 1, wherein the plurality of barbs is operable to penetrate and self-adhere to the tissue.

Statement 13. The device of Statement 1, wherein the receiver, the plurality of barbs, and the linking rod are biologically resorbable.

Statement 14. The device of Statement 1, wherein the device further comprises polyglactin, polydioxanone, polyglecaprone, poly-hydroxy-butyrate, calcium compounds, or other resorbable materials.

Statement 15. The device of Statement 1, wherein the device further comprises magnesium, titanium, nitinol, steel or other metals.

Statement 16. The device of Statement 1, wherein the diameter of the device is 2-100 mm.

Statement 17. The device of Statement 1, wherein each receiver contains four barbs.

Statement 18. The device of Statement 17, wherein the barbs are spaced 90 degrees relative to one another around the receiver.

Statement 19. The device of Statement 1, wherein each of the plurality of barbs extends at an angle of less than 90 degrees from the rod.

Statement 20. The device of Statement 1, wherein at least one of the plurality of barbs further comprises a blunted end.

Statement 21. A device for tissue closure, the device comprising: a rod; a plurality of barbs extending from the rod, each of the plurality of barbs comprising: a barb body; and a plurality of projections.

Statement 22. The device of Statement 21, wherein the device is operable to close tissue subcutaneously, trans-cutaneously, trans-fascially, trans-muscularly, across ligamentous tissue, across tendinous tissue, or across joint capular tissue.

Statement 23. The device of Statement 21, wherein the plurality of barbs is operable to penetrate and self-adhere to the tissue.

Statement 24. The device of Statement 21, wherein the rod and the plurality of barbs are biologically resorbable.

Statement 25. The device of Statement 21, wherein the device further comprises polyglactin, polydioxanone, polyglecaprone, poly-hydroxy-butyrate, calcium compounds, or other resorbable materials.

Statement 26. The device of Statement 21, wherein the device further comprises magnesium, titanium, nitinol, steel or other metals.

Statement 27. The device of Statement 21, wherein the rod has a cylindrical shape.

Statement 28. The device of Statement 26, wherein the diameter of the device is 2-100 mm.

Statement 29. The device of Statement 21, wherein the length of each of the plurality of projections is 0.25-10 mm.

Statement 30. The device of Statement 21, wherein each of the plurality of projections extends at an angle of less than 90 degrees from the barb body.

Statement 31. The device of Statement 30, wherein each of the plurality of projections extends at an angle of 45 degrees from the barb body.

Statement 32. The device of Statement 30, wherein each of the plurality of projections is angled toward the rod.

Statement 33. The device of Statement 21, wherein the plurality of barbs is attached to the rod in groups.

Statement 34. The device of Statement 33, wherein each group contains four barbs.

Statement 35. The device of Statement 34, wherein the barbs in each group are spaced 90 degrees relative to one another around the rod.

Statement 36. The device of Statement 21, wherein each of the plurality of barbs extends at an angle of less than 90 degrees from the rod.

Statement 37. The device of Statement 21, wherein the device is modular.

Statement 38. The device of Statement 21, wherein at least one of the plurality of barbs further comprises a blunted end.

Statement 39. A method of tissue closure, the method comprising: placing a device of Statement 1 or Statement 21 between edges of an opened tissue; and pressing the edges of the opened tissue on the device, wherein the barbs penetrate and are retained within the tissue.

Statement 40. The method of Statement 39, wherein the method further comprises pressing the device downward into tissues below the opened tissue.

What is claimed is:

1. A device for tissue closure comprising two or more subassemblies, each subassembly comprising:
   a receiver having a central opening and centerline axis;
   a plurality of barbs extending radially outward from the receiver; and
   a linking rod extending from the receiver along the centerline axis of the receiver, the linking rod comprising a locking end opposite the receiver,
   wherein the locking end of a first subassembly is configured to engage the receiver of a second subassembly,
   wherein the plurality of barbs further comprises a plurality of projections.

2. The device of claim 1, further comprising an end subassembly comprising:

a receiver having a central opening and centerline axis; and a plurality of barbs extending radially outward from the receiver.

3. The device of claim 1, wherein the linking rod further comprises a reinforcing bar extending radially outward from the linking rod.

4. The device of claim 1, wherein the locking end of the first subassembly and the receiver of the second subassembly comprise snap and lock mechanisms for coupling the subassemblies together.

5. The device of claim 1, wherein a length of each of the plurality of projections is 0.25-10 mm.

6. The device of claim 1, wherein each of the plurality of projections extends at an angle of less than 90 degrees from the barb.

7. The device of claim 1, wherein each of the plurality of projections extends at an angle of 45 degrees from the barb.

8. The device of claim 1, wherein each of the plurality of projections is angled toward the receiver.

9. The device of claim 1, wherein the device is operable to close tissue subcutaneously, transcutaneously, trans-fascially, trans-muscularly, across ligamentous tissue, across tendinous tissue, or across joint capular tissue.

10. The device of claim 1, wherein the plurality of barbs is operable to penetrate and self-adhere to the tissue.

11. The device of claim 1, wherein the receiver, the plurality of barbs, and the linking rod are biologically resorbable.

12. The device of claim 1, wherein the device further comprises polyglactin, polydioxanone, polyglecaprone, poly-hydroxy-butyrate, calcium compounds, or other resorbable materials.

13. The device of claim 1, wherein the device further comprises magnesium, titanium, nitinol, steel or other metals.

14. The device of claim 1, wherein a diameter of the device is 2-100 mm.

15. The device of claim 1, wherein each of the plurality of barbs extends at an angle of less than 90 degrees from the rod.

16. The device of claim 1, further comprising a second plurality of projections extending radially from the receiver having a blunted end.

17. A device for tissue closure comprising two or more subassemblies, each subassembly comprising:

a receiver having a central opening and centerline axis;

a plurality of barbs extending radially outward from the receiver; and a linking rod extending from the receiver along the centerline axis of the receiver, the linking rod comprising a locking end opposite the receiver, wherein the locking end of a first subassembly is configured to engage the receiver of a second subassembly, wherein the locking end of the first subassembly and the receiver of the second subassembly comprise twist and lock mechanisms for coupling the subassemblies together.

18. A device for tissue closure comprising two or more subassemblies, each subassembly comprising:

a receiver having a central opening and centerline axis;

a plurality of barbs extending radially outward from the receiver; and a linking rod extending from the receiver along the centerline axis of the receiver, the linking rod comprising a locking end opposite the receiver, wherein the locking end of a first subassembly is configured to engage the receiver of a second subassembly, wherein each receiver contains four barbs;

wherein the barbs are spaced about 90 degrees relative to one another around the receiver.

* * * * *